US010188609B2

(12) United States Patent
Tran et al.

(10) Patent No.: US 10,188,609 B2
(45) Date of Patent: Jan. 29, 2019

(54) MICROPARTICLES COMPRISING A PROBIOTIC, CROSS-LINKABLE REAGENT, A DENATURED PROTEIN, POLYOL PLASTICISER AND TREHALOSE

(71) Applicant: ProGel Pty Ltd, Brisbane (AU)

(72) Inventors: Lai Tran, Carina Heights (AU); Su Hung Ching, Banyo (AU); Cameron Turner, Rochedale South (AU); Bhesh Bhandari, Queensland (AU)

(73) Assignee: ProGel Pty Ltd, Brisbane (AU)

( * ) Notice: Subject to any disclaimer, the term of this patent is extended or adjusted under 35 U.S.C. 154(b) by 0 days.

(21) Appl. No.: 14/648,292

(22) PCT Filed: Nov. 29, 2013

(86) PCT No.: PCT/AU2013/001385
§ 371 (c)(1),
(2) Date: May 29, 2015

(87) PCT Pub. No.: WO2014/082132
PCT Pub. Date: Jun. 5, 2014

(65) Prior Publication Data
US 2015/0313844 A1 Nov. 5, 2015

(30) Foreign Application Priority Data
Nov. 29, 2012 (AU) ................. 2012905214

(51) Int. Cl.
*A61K 9/16* (2006.01)
*A61K 9/14* (2006.01)
*A61K 35/745* (2015.01)
*A23L 2/52* (2006.01)
*A23L 33/115* (2016.01)
*A23L 33/135* (2016.01)
*A23L 33/185* (2016.01)
*A23K 10/18* (2016.01)
*A23K 20/147* (2016.01)
*A23K 20/158* (2016.01)
*A23P 10/30* (2016.01)
*C12N 1/04* (2006.01)
*C12N 1/20* (2006.01)
*A61K 35/747* (2015.01)
*A61K 35/00* (2006.01)

(52) U.S. Cl.
CPC ............ *A61K 9/1694* (2013.01); *A23K 10/18* (2016.05); *A23K 20/147* (2016.05); *A23K 20/158* (2016.05); *A23L 2/52* (2013.01); *A23L 33/115* (2016.08); *A23L 33/135* (2016.08); *A23L 33/185* (2016.08); *A23P 10/30* (2016.08); *A61K 9/145* (2013.01); *A61K 9/146* (2013.01); *A61K 35/745* (2013.01); *A61K 35/747* (2013.01); *C12N 1/04* (2013.01); *C12N 1/20* (2013.01); *A23V 2002/00* (2013.01); *A23Y 2220/17* (2013.01); *A23Y 2300/49* (2013.01); *A61K 2035/115* (2013.01)

(58) Field of Classification Search
None
See application file for complete search history.

(56) References Cited

U.S. PATENT DOCUMENTS

| 2005/0191390 A1* | 9/2005 | Krochta ................. A23G 1/305 426/302 |
| 2007/0042184 A1 | 2/2007 | Coyne et al. |
| 2007/0160678 A1 | 7/2007 | Guimberteau et al. |
| 2008/0213441 A1 | 9/2008 | Ludwig et al. |
| 2008/0317799 A1 | 12/2008 | Baker |
| 2010/0173002 A1 | 7/2010 | Yulai et al. |
| 2012/0156252 A1 | 6/2012 | Brodkorb et al. |
| 2012/0263826 A1* | 10/2012 | Fang ...................... A23L 2/02 426/61 |
| 2013/0202740 A1 | 8/2013 | Given et al. |
| 2015/0299516 A1 | 10/2015 | Tran |
| 2015/0306038 A1 | 10/2015 | Tran et al. |

FOREIGN PATENT DOCUMENTS

| CN | 102210659 A | * 10/2011 |
| CN | 102210659 B | 7/2012 |
| JP | 2012-527898 A | 11/2012 |
| WO | WO 2004/009054 A2 | 1/2004 |
| WO | WO 2005/115341 A2 | 12/2005 |
| WO | WO 2006/122965 A1 | 11/2006 |
| WO | WO 2008/017962 A2 | 2/2008 |
| WO | WO 2008/120975 A1 | 10/2008 |

(Continued)

OTHER PUBLICATIONS

Eng. machine translation. Fan, D. et al. Chinese Patent Application Publication No. CN102210659(A). Oct. 12, 2011. Bifidobacterium microcapsule and preparing method thereof. specif. pp. 2, 3.*
Monahan, F.J. et al. 1995. Effect and temperature on protein unfolding and thiol/disulfide interchange reactions during heat-induced gelation of whey proteins. Journal of Agricultural Food Chemistry 43: 46-52. specif. p. 46.*

(Continued)

Primary Examiner — Renee Claytor
Assistant Examiner — Sharon M. Papciak
(74) Attorney, Agent, or Firm — Wolf, Greenfield & Sacks, P.C.

(57) ABSTRACT

The present invention relates to microparticles, methods of producing microparticles and microparticle precursor compositions. In particular, it relates to microparticles comprising a protective matrix and a protective matrix precursor composition comprising a blend of a denatured protein, a polyol plasticizer, trehalose and a carrier.

14 Claims, 5 Drawing Sheets

(56) References Cited

FOREIGN PATENT DOCUMENTS

| | | | | |
|---|---|---|---|---|
| WO | WO-2008120975 A1 * | 10/2008 | ........... | A61K 9/5052 |
| WO | WO 2009/062254 A1 | 5/2009 | | |
| WO | WO 2009/070012 A | 6/2009 | | |
| WO | WO 2010/111347 A2 | 9/2010 | | |
| WO | WO 2010/138522 A2 | 12/2010 | | |
| WO | WO 2010/149759 A1 | 12/2010 | | |
| WO | WO 2010138522 A2 * | 12/2010 | ............. | A23L 1/034 |
| WO | WO 2011/091111 A1 | 7/2011 | | |
| WO | WO 2011/094469 A2 | 8/2011 | | |
| WO | WO 2014/078912 A1 | 5/2014 | | |
| WO | WO 2014/082131 A1 | 6/2014 | | |
| WO | WO 2014/082132 A1 | 6/2014 | | |

OTHER PUBLICATIONS

Extended European Search Report for Application No. EP 13859362.9 dated Apr. 19, 2016.
Hansen et al., Survivial of Ca-alginate microencapsulated *Bifidobacterium* spp. in milk and simulated gastrointestinal conditions. Food Microbiology. 2002;19:35-45.
Kailasapathy, Microencapsulation of probiotic bacteria: technology and potential applications. Curr Issues Intest Microbiol. Sep. 2002;3(2):39-48. Review.
Sheu et al., Improving survival of culture bacteria in frozen desserts by microentrapment. J Dairy Sci. Jul. 1993;76(7):1902-7.
Extended European Search Report for EP Application No. 13856411.7 dated Jun. 22, 2016.
Extended European Search Report for EP Application No. 13858805.8 dated Jul. 5, 2016.
Office Communication for U.S. Appl. No. 14/647,340 dated Sep. 15, 2016.
Office Communication for U.S. Appl. No. 14/648,310 dated Jun. 2, 2016.
International Search Report and Written Opinion dated Feb. 5, 2014 in connection with Application No. PCT/AU2013/001363.
International Preliminary Report on Patentability dated Jun. 4, 2015 in connection with Application No. PCT/AU2013/001363.
International Search Report and Written Opinion dated Feb. 11, 2014 in connection with Application No. PCT/AU2013/001384.
International Preliminary Report on Patentability dated Jun. 11, 2015 in connection with Application No. PCT/AU2013/001384.
International Search Report and Written Opinion dated Feb. 11, 2014 in connection with Application No. PCT/AU2013/001385.
International Preliminary Report on Patentability dated Jun. 11, 2015 in connection with Application No. PCT/AU2013/001385.
Office Communication for U.S. Appl. No. 14/647,340 dated Jan. 12, 2017.
Office Communication for U.S. Appl. No. 14/648,310 dated Jan. 5, 2017.
[No Author Listed], Dictionary of Chemical Engineering. Discontinuous phase. Oxford University Press. First Edition. Copyright 2014. Ed. Carl Schaschke. Oxford, UK. p. 110.
[No Author Listed], Dictionary of Food Science and Technology. Vitamin A. Wiley-Blackwell. Second Edition. Copyright 2009. International Food Information Service. Editorial Offices. Ames, Iowa. p. 445.

Boye et al., Food Proteins and their Applications. Excerpt from Chapter 2—Thermal Denaturation and Coagulation of Proteins. Eds. Srinivasan Damodaran, Alain Paraf. Marcel Dekker, Inc. New York. 1997. pp. 25-26, 8.
Office Communication for AU Application No. 2013350329 dated Jul. 14, 2016.
Office Communication for AU Application No. 2013350329 dated Jun. 21, 2017.
Office Communication for AU Application No. 2013350329 dated Jul. 6, 2017.
Office Communication for AU Application No. 2013351920 dated Aug. 17, 2017.
Office Communication for EP Application No. 13858805.8 dated Jun. 21, 2017.
Office Communication for JP Application No. 2015-544274 dated Jul. 4, 2017.
Office Communication for AU Application No. 2013351919 dated Sep. 20, 2017.
Office Communication for EP Application No. 13859362.9 dated Apr. 7, 2017.
He et al., Food proteins as novel nanosuspension stabilizers for poorly water-soluble drugs. International Journal of Pharmaceutics. 2013;441:269-78. Epub Nov. 27, 2012.
Hottiger et al., The role of trehalose synthesis for the acquisition of thermotolerance in yeast. II. Physiological concentrations of trehalose increase the thermal stability of proteins in vitro. Eur. J. Biochem. 1994;219:187-93.
Jain et al., Effect of trehalose on protein structure. Protein Science. 2009;18:24-36. Epub Dec. 2, 2008.
Office Communication for U.S. Appl. No. 14/647,340 dated Aug. 31, 2017.
Mills et al., Enhancing the stress responses of probiotics for a lifestyle from gut to product and back again. Microbial Cell Factories. 2011;10(Suppl 1):S19. 15 pages. Epub Aug. 30, 2011.
Teixeira et al., Identification of sites of injury in Lactobacillus bulgaricus during heat stress. Journal of Applied Microbiology. Jul. 1997;83(2):219-26.
Woojin et al., Assessment of Stress Response of the Probiotic *Lactobacillus acidophilus*. Current Microbiology. Nov. 2001;43(5):346-50, Kim et al.
Office Communication for AU Application No. 2013351920 dated Jul. 17, 2018.
Office Communication for JP Application No. 2015-544274 dated Jun. 5, 2018.
Office Communication for AU Application No. 2017204844 dated Feb. 20, 2018.
Office Communication for U.S. Appl. No. 14/648,310 dated Dec. 14, 2017.
Dorobantu et al., Stabilization of oil-water emulsions by hydrophobic bacteria. Appl Environ Microbiol. Oct. 2004;70(10):6333-6.
Kokkinos et al., Cell size of various lactic acid bacteria as determined by scanning electron microscope and image analysis. Lait. 1998;78:491-500.
Singer et al., Multiple Effects of Trehalose on Protein Folding in Vitro and In Vivo. Molecular Cell. Apr. 1998;1:639-48.
Xin et al., Influence of Lactobacillus E1 on the Storage Stability in Emulsion Immobilization. Journal of Wuhan University of Technology—Mater. Sci. Ed. Feb. 2009:75-80.

* cited by examiner

MICROPARTICLES COMPRISING A PROBIOTIC, CROSS-LINKABLE REAGENT, A DENATURED PROTEIN, POLYOL PLASTICISER AND TREHALOSE

RELATED APPLICATIONS

This application is a U.S. National Stage application of International Patent Application No. PCT/AU2013/001385, filed Nov. 29, 2013, entitled "Microparticles Comprising a Probiotic, Cross-Linkable Reagent, a Denatured Protein, Polyol Plasticiser and Trehalose," which claims priority to Australian Application Serial No. AU 2012905214, filed Nov. 29, 2012, entitled "Microparticles and methods of producing microparticles," the contents of which are incorporated herein by reference in their entirety.

TECHNICAL FIELD

The present invention relates to microparticles, methods of producing microparticles and microparticle precursor compositions.

BACKGROUND

In a healthy gut, there is a balance between beneficial and pathogenic bacteria. Various factors including food, stress, illness or infection and medications can disrupt this balance leading to an excess of pathogenic bacteria. This imbalance may lead to bloating, gas and constipation. Over recent years, there has been a significant increase in the use of probiotic micro-organisms (hereinafter "probiotics") to address this imbalance. It is believed that probiotics can inhibit or influence the growth and/or metabolism of pathogenic bacteria in the intestinal tract. Probiotics may also activate immune function. For this reason, there is considerable interest in incorporating probiotics into nutritional supplements or foodstuffs.

There are difficulties associated with incorporating probiotics into nutritional supplements or foodstuffs. One primary difficulty is having or maintaining an adequate number of viable micro-organisms in the relevant product. If the concentration of the viable probiotics in the food product does not exceed a certain threshold value, the beneficial effect of the probiotics is not provided. Temperature and exposure to oxygen, water and acids can affect probiotic viability. Furthermore, the shear forces generated in certain production processes such as high-speed blending, emulsification and homogenization may result in cell disruption and losses in viability. This sensitivity can make it difficult to incorporate probiotics into products and to combine probiotics with other actives to produce products with added beneficial activity.

Products including the probiotics must be palatable to the consumer. Probiotics can have flavours that may be perceived by the human or animal ingesting the product as being unpleasant. Actives that may be used in conjunction with probiotics may also have flavours capable of being perceived as objectionable.

There has been some interest in providing probiotics in microparticles. Microencapsulation is a process in which thin films or coatings or solid/gel matrix surround, enclose and/or immobilise tiny particles or droplets of the one or more actives, such as a probiotic. The resultant microparticles are typically spherical in shape and contain active material surrounded by a continuous wall or trapped in the solid or gel matrix. Microencapsulation provides the one or more actives in a finely divided state.

The encapsulated probiotic may be protected from degradation by limiting its exposure to the external environment (e.g. heat, moisture, acid, air, light) and may be released at a controlled rate under specific conditions as desired. However, often the encapsulation material is porous. Thus, the encapsulated probiotic may nevertheless be exposed to a degrading exterior environment. Also, the probiotic may leak out of the porous microparticle and any flavour associated with the probiotic may emanate from the microparticle and be perceived by the person or animal ingesting it.

It can be desirable to combine a probiotic with one or more other actives to produce a microparticle with added beneficial activity. These other actives may be susceptible to degradation and it is desirable to provide a microparticle with suitable barrier properties for limiting exposure of the active to degrading elements from the external environment. Furthermore, certain actives may be rendered stable through encapsulation by providing a microparticle with suitable barrier properties. Also, similarly to the probiotic, other actives may have flavours that can be perceived by the consumer as being objectionable. Thus, it is also desirable to provide a microparticle with suitable barrier properties for masking any flavour of the active. As noted above, encapsulation materials are often porous and the encapsulated active may be exposed to a degrading exterior environment or leak out of the porous microparticle. This leakage can lead to the flavour associated with the active being perceived by the person or animal ingesting it.

When preparing a microparticle precursor composition, it can be difficult to combine the probiotic with other actives due to the sensitivity of the probiotic. Blending any other actives with the remaining components of the microparticle precursor composition, including the probiotic, can involve shear rates that disrupt the cells of the probiotic and compromise its viability.

An opportunity therefore remains to address or ameliorate one or more shortcomings or disadvantages associated with existing methods of incorporating probiotics into microparticles and combining probiotics with other actives and/or to at least provide a useful alternative thereto.

SUMMARY OF THE INVENTION

The present invention provides a microparticle precursor composition comprising a blend of a probiotic, a cross-linkable reagent, a denatured protein, a polyol plasticizer, trehalose and a carrier. In some embodiments, the blend further comprises an emulsion comprising a hydrophobic active.

The invention also provides a protective matrix precursor composition comprising a blend of a denatured protein, a polyol plasticizer, trehalose and a carrier. Also, a method of producing a protective matrix precursor composition comprising blending together a denatured protein, a polyol plasticizer, trehalose and a carrier is provided.

In addition, the present invention provides method of producing a microparticle precursor composition comprising blending together a probiotic, the protective matrix precursor composition and a cross-linkable reagent. In some embodiments, the method comprises: blending the probiotic with the protective matrix precursor composition to form a probiotic-containing matrix precursor; blending an emulsion comprising a hydrophobic active with the probiotic-containing matrix precursor to form a probiotic-containing emulsion; and blending the probiotic-containing emulsion with a cross-linkable reagent. A microparticle precursor composition produced according to this method is also provided.

The present invention further provides a method of producing microparticles comprising: providing the microparticle precursor composition of the present invention in a finely divided state; and exposing the finely divided microparticle precursor composition to a cross-linking reagent that reacts with the cross-linkable reagent of the microparticle precursor composition to form microparticles.

Microparticles produced according to the method of the present invention are also provided.

These and other aspects of the invention, including a product comprising microparticles according to the present invention are described in more detail below.

DETAILED DESCRIPTION

Figure 1:
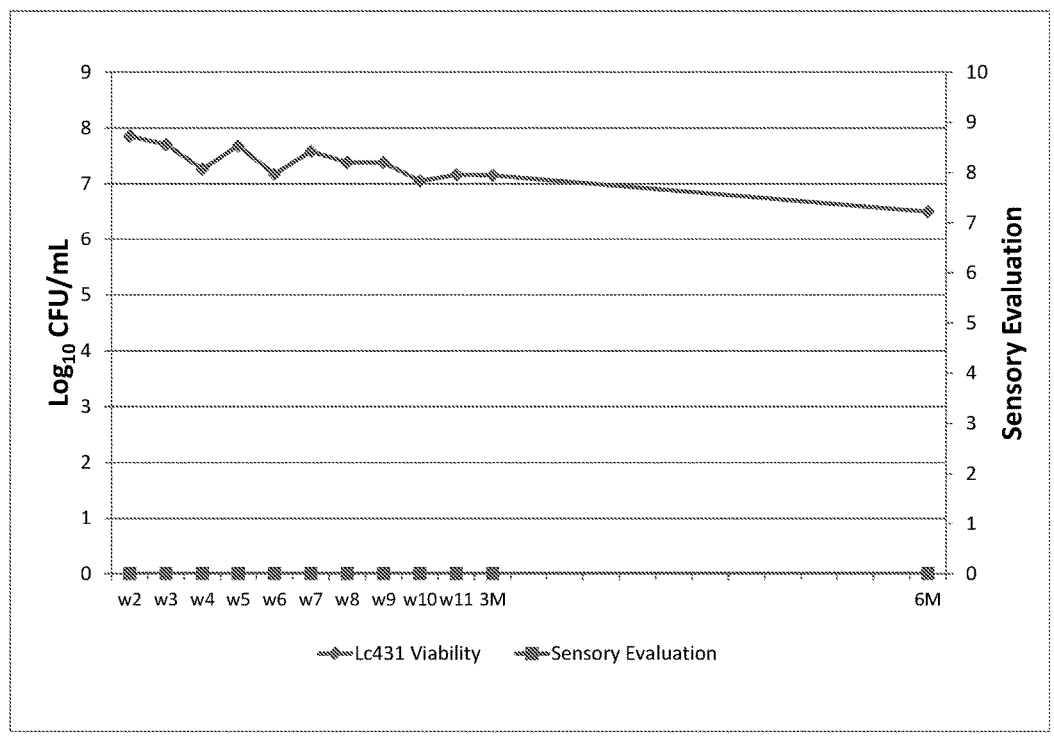
FIG. 1 shows the results of probiotic survival and flavor perception tests described in Example 15.

The present invention provides a protective matrix which may be used to enhance the viability of a probiotic distributed within it. A microparticle precursor composition in accordance with the present invention comprises blend of a probiotic, a cross-linkable reagent, a denatured protein, a polyol plasticizer, trehalose and a carrier. It will be appreciated that the microparticle precursor composition typically comprises a protective matrix precursor composition comprising a blend of a denatured protein, a polyol plasticizer, trehalose and a carrier. That is, these components (e.g. a polyol plasticizer, trehalose, a denatured protein and carrier) are starting materials or ingredients which, when suitably combined, interact and bond to produce the protective matrix of the present invention. As will be discussed in further detail below, a number of synergistic interactions occur between the components of the protective matrix in order to provide a matrix with desirable properties. These interactions may take advantage of the hydrophilic and hydrophobic character of the denatured protein to form beneficial hydrogen and hydrophobic bonds, and the ability of trehalose to stablise the protein and the probiotic, as well as any other actives distributed within the protective matrix.

The present invention particularly relates to microparticles that are intended to be ingested by humans, but potentially other animals. Accordingly, it will be appreciated by the skilled person that the ingredients of the microparticles of the present invention are selected such that they are fit for purpose. That is, in the case of a microparticle intended to be ingested by humans, the ingredients of the microparticle are approved for human consumption by any necessary authorities. Likewise, for products intended for animal consumption, the ingredients will be approved for such use. By way of example, the present invention is generally described with reference to microparticles intended for human consumption.

In general, components that are fit for human consumption may be considered edible or food-grade. That is, the components are intended to be consumed and they are not merely in a nontoxic form which is ancillary to their ultimate and intended purpose.

The present invention provides a product comprising the microparticles. For example, the microparticles produced in accordance with the present invention may be used in pharmaceutical or nutritional formulations (e.g. nutraceuticals), dietary supplements, functional foods and beverage products. Thus, in some embodiments, there is provided a product that has been supplemented (fortified) with the microparticles of the present invention. In some embodiments, food and beverages for humans as well as animals (e.g. pet food) may be supplemented using inventive microparticles containing one or more desirable actives, namely: at least a probiotic and potentially one or more other actives. Suitable examples of beverage products include, but are not limited to, water; milk; milk alternatives including, but not limited to, soy, rice, oat and almond "milks"; water-based beverages; milk-based beverages; carbonated beverages; non-carbonated beverages; beer; wine; and fruit and/or vegetable-based beverages.

Suitable fruit and/or vegetable-based beverages may include one or more fruit extracts and/or vegetable extracts. An extract includes juice, nectar, puree and/or pulp of or from the relevant fruit or vegetable. The extract may be fresh, raw, processed (e.g. pasteurized) or reconstituted. The one or more fruit extracts may be selected from, but are not limited to, the group comprising apple juice, pineapple juice, one or more citrus fruit juices (i.e. one or more juices of orange, mandarin, grapefruit, lemon, tangelo, cumquat, etc.), cranberry juice, noni juice, acai juice, goji juice, blueberry juice, blackberry juice, raspberry juice, pomegranate juice, grape juice, apricot juice or nectar, peach juice or nectar, pear juice, mango juice, passionfruit juice and guava puree. The one or more vegetable extracts may be selected from, but are not limited to, the group comprising aloe vera juice, beet juice, carrot juice, celery juice, kale juice, spinach juice, tomato juice and wheat grass juice. Furthermore, vegetable extracts may include extracts of herbs or spices, such as ginger juice.

Up to 10 grams of microparticles may be added per kilogram or per liter of product to be supplemented with the probiotic. For example, from about 7 grams to about 9 grams of microparticles may be added per kilogram or per liter of product to be supplemented. About 8 grams of microparticles may be added per kilogram or per liter of product to be supplemented. In some embodiments, 8 grams of microparticles are added per liter of juice, such as fresh orange juice, to be supplemented.

In some supplemented products, such as a liquid sweet formulation, the amount of microparticles in the product may represent up to 13% of the product weight.

In some embodiments, the product supplemented with the microparticles is a powder. For example, in some embodiments the product is a meal replacement protein powder. In these embodiments, microparticles may be added to the powder product at a microparticle:powder (i.e. other product components) ratio, by weight, of up to 1:9. For example, in some embodiments, microparticles are added at a ratio of 1:49. In some other embodiments, the ratio is about 1:9.

In some embodiments, the primary constituent of the product will be the microparticles. In some such embodiments, the microparticles may be 51% or more of the product weight. For example, products in which up to 72% of the product weight is microparticles may be produced. Such products may be pharmaceutical or nutritional formulations (e.g. nutraceuticals).

Probiotics are defined as live microbes that beneficially affect the human or animal that has ingested it by modulating mucosal and systemic immunity, as well as improving intestinal function and microbial balance in the intestinal tract. Probiotics can exhibit one or more of the following non-limiting characteristics: non-pathogenic or non-toxic to the host; are present as viable cells, preferably in large numbers; capable of survival, metabolism, and persistence in the gut environment (e.g., resistance to low pH and gastrointestinal acids and secretions); adherence to epithelial cells, particularly the epithelial cells of the gastrointestinal tract; microbicidal or microbistatic activity or effect toward pathogenic bacteria; anticarcinogenic activity; immune modulation activity, particularly immune enhancement; modulatory activity toward the endogenous flora; enhanced urogenital tract health; antiseptic activity in or around wounds and enhanced would healing; reduction in diarrhea; reduction in allergic reactions; reduction in neonatal necrotizing enterocolitis; reduction in inflammatory bowel disease; and reduction in intestinal permeability.

The probiotic used as an active in the present invention may be selected from, but not limited to, the group consisting of yeasts such as *Saccharomyces, Debaromyces, Candida, Pichia* and *Torulopsis*, moulds such as *Aspergillus, Rhizopus, Mucor,* and *Penicillium* and bacteria such as the genera *Bifidobacterium, Bacteroides, Clostridium, Fusobacterium, Melissococcus, Propionibacterium, Streptococcus, Enterococcus, Lactococcus, Staphylococcus, Peptostrepococcus, Bacillus, Pediococcus, Micrococcus, Leuconostoc, Weissella, Aerococcus, Oenococcus* and *Lactobacillus*, as well as combinations thereof.

Examples of suitable probiotics include: *Saccharomyces cereviseae* (*boulardii*), *Bacillus coagulans, Bifidobacterium animalis, Bifidobacterium bifidum, Bifidobacterium breve, Bifidobacterium infantis, Bifidobacterium longum, Bifidobacterium lactis, Enterococcus faecium, Enterococcus faecalis, Lactobacillus acidophilus, Lactobacillus alimentarius, Lactobacillus casei* subsp. *casei, Lactobacillus casei Shirota, Lactobacillus curvatus, Lactobacillus delbruckii* subsp. *lactis, Lactobacillus farciminus, Lactobacillus fermentum, Lactobacillus gasseri, Lactobacillus helveticus, Lactobacillus johnsonii, Lactobacillus paracasei, Lactobacillus plantarum, Lactobacillus reuteri, Lactobacillus rhamnosus* (*Lacrobacillus* GG), *Lactobacillus sake, Lactobacillus salivarius, Lactococcus lactis, Pediococcus acidilactici, Pediococcus pentosaceus, Pediococcus acidilactici, Pediococcus halophilus, Streptococcus faecalis, Streptococcus thermophilus* and *Saccharomyces boulardii*. More specifically the probiotic may selected from the group comprising of *Lactobacillus casei* Lc431, *Lactobacillus rhamnosus* CGMCC 1.3724, *Bifidobacterium lactis* BB12, *Bifidobacterium lactis* CNCM I-3446, *Bifidobacterium longum* ATCC BAA-999, *Lactobacillus paracasei* CNCM I-2116, *Lactobacillus johnsonii* CNCM I-1225, *Lactobacillus fermentum* VRI 003, *Bifidobacterium longum* CNCM I-2170, *Bifidobacterium longum* CNCM I-2618, *Bifidobacterium breve, Lactobacillus paracasei* CNCM I-1292, *Lactobacillus rhamnosus* ATCC 53103, *Enterococcus faecium* SF 68, *Lacrobacillus reuteri* ATCC 55730, *Lactobacillus reuteri* ATCC PTA 6475, *Lactobacillus reuteri* ATCC PTA 4659, *Lacrobacillus reuteri* ATCC PTA 5289, *Lactobacillus reuteri* DSM 17938, and mixtures thereof. In some preferred embodiments, the microparticle may contain *Lactobacillus casei* Lc431 or *Bifidobacterium lactis* BB12.

The probiotic is viable if it is alive and capable of reproduction or colonization. The concentration of viable probiotics in the microparticle must exceed a certain threshold value or the beneficial effect of the probiotics is not provided. Quantities of probiotics are typically evaluated in terms of colony forming units (CFU). Typically, dosages of about one to two million CFU are required for adult humans to receive the beneficial effects of the probiotic. So that these sorts of dosages may be achieved, the loading of viable probiotic in the microparticle is often in the order of five to ten billion CFU/g, for example about 2.5% to about 5% of the microparticle weight. In some embodiments, the loading of probiotic is around 2.5% of the microparticle weight. In some other embodiments, the loading of probiotic may be around 4% of the microparticle weight.

In some embodiments, the microparticle may comprise one or more actives in addition to the probiotic. Suitable additional actives may be selected from a variety of functional substrates that are conventionally provided in microencapsulated form for consumption or other use as might be necessary. Such actives include:
  animal feed supplements;
  oils, such as fish oils e.g. (omega-3);
  pharmaceuticals, such as ibuprofen and gentamicin;
  enzymes, such as lysozymes and insulin; and
  vitamins, such as vitamins A, E, D, K1, B12, B9, B1 and B6.

Certain actives that may be used in addition to the probiotic may be hydrophobic actives. Hydrophobic actives are active compounds that are generally immiscible in water. These actives may be lipids or actives that are provided in a solution with a water immiscible solvent. This water immiscible solvent may be a lipid.

Hydrophobic actives that are lipids include nutritional oils, such as fish oil. As used herein, the term "fish oil" means oil derived from fish and/or other marine organism(s). For example, fish oil includes oil derived from krill, calamari (squid), caviar, abalone scallops, anchovies, catfish, clams, cod, herring, lake trout, mackerel, menhaden, orange roughy, salmon, sardines, pilchards, sea mullet, sea perch, shark, shrimp, trout and tuna, and combinations thereof.

Fish oil is a source of omega-3 fatty acid. Other sources of omega-3 fatty acid include, but are not limited to, plant-based oils that are rich in omega-3 fatty acids such as, walnut, linseed (flaxseed), rapeseed (canola), chia (typically *Salvia hispanica*) seed and hemp seed oils. Thus, sources of omega-3 fatty acids may be hydrophobic actives for the purposes of the present invention.

When a source of omega-3 fatty acid is a fish oil or plant-based oil, the oil may be a crude oil, a partially refined oil, a refined oil, or an oil concentrate.

In some embodiments, such as when the active is a source of omega-3 fatty acid (e.g. fish oil), the amount of hydrophobic active in the microparticle may represent up to 20% of the microparticle weight. In some embodiments, the amount of hydrophobic active may be around 10% of the microparticle weight.

The term "omega-3 fatty acid" means a long chain polyunsaturated fatty acid having a carbon-carbon double bond between the third and fourth carbon from the methyl terminus of the fatty acid chain. Common omega-3 fatty acids include alpha linolenic acid (C18:3; (9Z,12Z,15Z)-Octadeca-9,12,15-trienoic acid, "ALA"), eicosapentaenoic acid (C20:5; (5Z,8Z,11Z,14Z,17Z)-icosa-5,8,11,14,17-pentaenoic acid, "EPA"), and docosahexaenoic acid (C22:6; (4Z,7Z,10Z,13Z,16Z,19Z)-docosa-4,7,10,13,16,19-hexaenoic acid, "DHA"). Other common omega-3 fatty acids include, but are not limited to, stearidonic acid (C18:4), eicosatetraenoic acid (C20:4), and docosapentaenoic acid (C22:5).

Other oils that are hydrophobic actives for the purposes of the present invention include, but are not limited to, avocado oil, apricot kernel oil, argan oil, evening primrose oil, garlic oil and peppermint oil.

The hydrophobic active may be a lipid-soluble vitamin. Lipid-soluble vitamins which may be used in this invention include vitamins A, vitamins D, vitamins E, vitamins K, and ubiquinones, for example.

The vitamins A include vitamins A such as retinol (vitamin $A_1$ alcohol), retinal (vitamin $A_1$ aldehyde), vitamin $A_1$ acid, 3-dehydroretinol (vitamin $A_2$ alcohol), and 3-dehydroretinal (vitamin $A_2$ aldehyde) and provitamins A such as β-carotene (β,β-carotene), α-carotene (β, ε-carotene) and γ-carotene (β, ψ-carotene), for example. A provitamin A, such as β-carotene, may be a particularly preferred active for incorporation into the microparticle of the present invention. In some embodiments, β-carotene may be used in combination with a probiotic and fish oil.

The vitamins D include vitamins D such as vitamin $D_2$, vitamin $D_3$, vitamin $D_4$, vitamin $D_5$, vitamin $D_6$, and vitamin $D_7$ and provitamins thereof, for example.

The vitamins E include tocopherols such as α-tocopherol, β-tocopherol, γ-tocopherol, and δ-tocopherol and tocotrienols such as α-tocotrienol, β-tocotrienol, γ-tocotrienol, and δ-tocotrienol, for example.

The vitamins K include vitamin $K_1$ and vitamins $K_2$, for example.

The ubiquinones include ubiquinone-1 to ubiquinole-12 (Q-1 to Q-12) and the oxidized forms thereof and amino chloride compounds thereof, for example.

Hydrophobic actives, such as lipid-soluble vitamins, will typically be dissolved in a lipid (acting as a water immiscible solvent) in order to put them into a form suitable for use in the present invention. Lipids may be oils, waxes, fatty acids, fatty alcohols, monoglycerides and triglycerides, which are either saturated or unsaturated. In some embodiments, a blend of lipids may be used.

In general, the lipid or lipids selected for dissolving the hydrophobic active will be liquid. That is, a lipid that has a melting point of 25° C. or less, preferably 10° C. or less. In some embodiments, it is preferred that the lipid has a melting point lower than the storage temperature of the microparticle. Liquid lipids are often selected as they may be more readily emulsified with other components to form the emulsion comprising the hydrophobic active. Solid lipids may need to be heated to above their melting temperature or dissolved in a suitable solvent, which may be another lipid, in order to be effectively combined with the active. Typically, if solid lipids are used, they are first blended with a suitable solvent (such as a liquid lipid) so as to produce a lipid mixture that is liquid at 25° C. or less, preferably 10° C. or less.

Liquid lipids may also be more readily digested by the human or animal ingesting the microparticle. Thus, the selection of a liquid lipid may be useful to ensure that any actives dissolved in the lipid are released at an optimum time.

Lipids used in embodiments of the invention can be derived from many different sources.

In some embodiments, lipids used in embodiments of the invention can include biological lipids. Biological lipids can include lipids (fats or oils) produced by any type of plant, such as vegetable oils, or animal. In one embodiment, the biological lipid used includes triglycerides.

Many different biological lipids that are derived from plants may be used, and these plants may be genetically modified crops. By way of example, plant-based lipids can include soybean oil, canola oil, cottonseed oil, grape seed oil, mustard seed oil, corn oil, linseed oil, safflower oil, sunflower oil, poppy seed oil, pecan oil, walnut oil, peanut oil, rice bran oil, *camellia* oil, olive oil, palm oil, palm kernel oil and coconut oil, or combinations thereof. Other plant-based lipids can be obtained from almond, argan, avocado, babassu, beech, ben (from the seeds of the *Moringa oleifera*), borneo tallow nut, brazil nut, camelina, caryocar (pequi), cashew nut, cocoa, cohune palm, coriander, cucurbitaceae (e.g. butternut squash seed oil, pumpkin seed oil and watermelon seed oil), hemp, kenaf, macadamia, noog *abyssinia, perilla*, pili nut, *quinoa*, sacha inchi, seje, sesame, shea nut, tea seed and *papaya* seed. These may be used alone or in combination with another lipid.

Lipids derived from animals may also be used, for example, white grease, lard (pork fat), tallow (beef fat), anhydrous milk fat, and/or poultry fat may be used. However, as noted above, liquid lipids with a melting point of 25° C. or less are preferred.

The lipid may be synthetic triglyceride of the formula

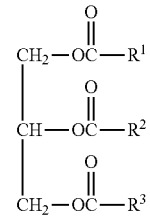

wherein $R^1$, $R^2$ and $R^3$ may be the same or different and are aliphatic hydrocarbyl groups that contain from 7 to about 23 carbon atoms. The term "hydrocarbyl group" as used herein denotes a radical having a carbon atom directly attached to the remainder of the molecule.

The aliphatic hydrocarbyl groups include the following:
(1) Aliphatic hydrocarbon groups; that is, alkyl groups such as heptyl, nonyl, undecyl, tridecyl, heptadecyl; alkenyl groups containing a single unsaturated bond such as heptenyl, nonenyl, undecenyl, tridecenyl, heptadecenyl, heneicosenyl; alkenyl groups containing plural unsaturated bonds; and all isomers thereof.
(2) Substituted aliphatic hydrocarbon groups containing non-hydrocarbon substituents, such as hydroxy of carbalkoxy groups.
(3) Hetero groups; that is, groups which, while having predominantly aliphatic hydrocarbon character, contain atoms other than carbon, such as oxygen, nitrogen or sulfur, present in a chain or ring otherwise composed of aliphatic carbon atoms.

Many biological lipids need to be processed following extraction from their natural source in order to remove impurities. For example, the lipids may be degummed to remove phospholipids, bleached to remove impurities and minor components such as chlorophyll and carotenoids that can give colour to the oil and fractionated to remove the free fatty acids that can give an undesirable taste and/or smell to the refined oil. "Fractionating" and related terms, as used herein, refer to a process in which less volatile components are separated from more volatile components, typically comprising the separation of triglycerides from free fatty acids in plant-derived biological lipids (oils).

Processing can include hydrogenation of the lipid. In this process, the lipid is hydrogenated by reducing the unsaturated bonds in the lipid. This usually achieved by exposing the lipid to hydrogen in the presence of a catalyst, such as a nickel catalyst. Hydrogenation may be complete or partial. A partially hydrogenated lipid may include a blend of unhydrogenated lipid and fully hydrogenated lipid.

Hydrogenating the lipid can be advantageous as it reduces the lipid's sensitivity to oxidation. Some lipids are particularly susceptible to oxidation, leading to them going rancid and producing an objectionable flavour, and hydrogenation of these lipids may be useful. However, hydrogenation can increase the melting point of the lipid, thus transforming a liquid lipid into a solid one, which can affect the ease with which the lipid may be blended with other components of the composition. Accordingly, the degree to which a lipid may be hydrogenated will be selected bearing in mind the impact any increase in melting point will have on the ease with which the lipid can then be used to dissolve the hydrophobic active.

Preferably, the lipid may be a plant-based lipid selected from the group consisting of: almond oil, canola oil, cod liver oil, corn oil, cotton seed oil, flaxseed oil, grape seed oil, peanut oil, safflower oil, sesame oil, soybean oil, sunflower oil, walnut oil, coconut oil or palm kernel oil. It will appreciated that, in some embodiments, a hydrophobic active (for example a lipid-soluble vitamin) may be dissolved in a lipid that constitutes a hydrophobic active in of itself (for example an oil rich in omega-3 fatty acids, such as flaxseed oil).

The microparticles of the present invention are typically spherical. Accordingly, they often have diameters in the order of 10 μm to 50 μm. In general, the microparticles have at least one dimension that is less than 1000 μm. However, the microparticles of the present invention are typically small and have at least one dimension that is less than 50 μm.

The microparticles according to the present invention may be manufactured by providing a cross-linkable microparticle precursor composition in a finely divided state and contacting it with a cross-linking reagent. Herein the term "cross-link" (and variations thereof) generally refers to a chemical link between two or more polymeric chains of atoms. A cross-linkable microparticle precursor composition in accordance with the invention comprises a cross-linkable reagent. The cross-linkable reagent can be a molecule, typically a polymer incorporating repeat units, that includes groups or moieties that can be cross-linked. Cross-links bind molecules together into a network, forming a larger molecular superstructure. The cross-links may be ionic, dative, complexation and coordination linkages, covalent, and may also involve hydrogen-bonding interactions. Thus, an ionically cross-linkable polymer, therefore, is generally a polymeric molecule that is capable of forming cross-links by reaction with an ionically cross-linking reagent so as to form microparticles. Ionic cross-links may be reversible or irreversible. An ionically cross-linkable reagent has one or more ionisable groups. The term "ionisable group" refers to a chemical moiety capable of partial or full ionisation.

The cross-linkable reagent may be a basic polyelectrolyte (poly base), basic ionomer, acidic polyelectrolyte (poly acid), or an acidic ionomer. In some embodiments, the cross-linkable reagent is selected from one or more anionic monomers or polycations. As used herein, the term "polycation" or related terms such as "cationic polymer" refer to a polymer composed of positively charged macromolecules. In some embodiments, the cross-linkable reagent is selected from one or more anionic monomers or polyanions.

Suitable cross-linkable polymers may be selected from the class of hydrogels including hydrocolloids. Hydrocolloids are hydrophilic polymers, of vegetable, animal, microbial or synthetic origin, that generally contain many hydroxyl groups and may be polyelectrolytes. Hydrocolloids which are not ionically cross-linkable may be used in blends with polymers which are ionically cross-linkable.

Polymers which may be used in the present invention include but are not limited to one or a mixture of polymers selected from the group consisting of polyvinyl alcohol, alginates, carrageens, pectins, carboxy methyl cellulose, hyaluronates, heparins, heparin sulfates, heparans, chitosans, carboxymethyl chitosan, agar, gum arabic, pullulan, gellan, xanthan, tragacanth, carboxymethyl starch, carboxymethyl dextran, chondroitins including chondroitin sulfate, dermatans, cationic guar and locust bean, konjac, gum ghatti, xyloglucans, karaya gums, cationic starch as well as salts and esters thereof.

Exemplary anionic polymers include one or a mixture of alginates, pectins, carboxy methyl cellulose, hyaluronates. Exemplary cationic polymers include chitosan, cationic guar, and cationic starch.

The ionically cross-linkable polymers from which the microparticles of this invention may be produced may be functionalised with carboxylic, sulfate, phosphate, sulphonamido, phosphonamido, hydroxy and amine functional groups.

The cross-linking reagent may be as a solution of an inorganic salt. Generally, suitable cross-linking reagents are solutions of dissolved ions. The cross-linking ions used to cross-link the cross-linkable reagent may be anions or cations depending on whether the cross-linkable reagent is anionically or cationically cross-linkable. Appropriate biocompatible cross-linking ions include but are not limited to cations selected from the group consisting of calcium, magnesium, barium, strontium, zinc, boron, beryllium, aluminium, iron, copper, cobalt, nickel, lead and silver ions, or mixtures of any two or more thereof. Anions may be selected from but are not limited to the group consisting of carboxylate, phosphate, sulphate, oxalate, bicarbonate, and carbonate ions. More broadly, the anions are derived from polybasic organic or inorganic acids. Preferred cross-linking cations are calcium ions.

In a preferred embodiment of the present invention, formation of the microparticles takes place by a sol-gel phase transition and the reagents used in this embodiment should be selected accordingly. Thus, in principle the cross-linkable reagent blended with other components of the microparticle precursor composition and cross-linking reagent may be selected from any suitable combination that will result in formation of microparticles by a sol-gel phase transition associated with the cross-linkable reagent. This said, the compatibility of the reagents with active(s) (i.e. the probiotic and any other active) incorporated into the microparticle, and the release characteristics of such actives when present in the microparticles will also need to be considered. Accordingly, the selection of the reagents will also depend upon the ultimate use of the microparticle and other components may be included, including the components of the protective matrix, in order to optimise the stability of the active(s) for the intended period of use.

The present invention will be described for the purposes of (non-limiting) illustration with reference to the use of alginates as the cross-linkable reagent. Alginates are particularly preferred for use in the invention because they are physiologically acceptable and they form thermally stable gels after binding with a suitable cation. Ionic gelation of alginates is based on their affinity towards and ability to bind certain ions. Alginates form strong, stable gels with divalent cations such as $Ca^{2+}$, $Sr^{2+}$, $Zn^{2+}$, $Co^{2+}$ and $Ba^{2+}$. Trivalent cations, such as $Fe^{3+}$ and $Al^{3+}$, may also effect gelling. There is no gelation with monovalent cations.

The use of alginate gels in the present invention is also advantageous since these gels may exhibit desirable active release characteristics. For example, alginate gels show stability in low pH conditions as they shrink and do not swell and disintegrate. Active release is therefore also low. On the other hand, alginate gels swell rapidly and show dissolution and/or disintegration in weak alkaline conditions. This property enables alginate gels to be used effectively to deliver probiotics and other actives to the human intestine (pH above 6.7). Alginate gels are also muco-adhesive and tend to stick to the intestinal mucosa for prolonged periods. Thus, the use of alginate gels may be particularly, advantageous for the delivery of certain actives, such as probiotics.

A number of factors influence alginate gel formation and these may need to be considered when implementing the present invention. One factor is the prevalence and length of gluconate (G) residues against the prevalence and length of mannuronate (M) residues. The M/G ratio is an important factor, at least in relation to $Ca^{2+}$ cross-linking. As the M/G ratio decreases, the requirement for $Ca^{2+}$ ion concentration increases for effective cross-linking. Gels formed from alginates with a high G content also tend to be stiffer, more brittle, and more porous and maintain strength and integrity for longer periods of time. Such gels do not swell excessively on cross-linking. Alginates with a high M content tend to form softer, less porous elastic gels with high shrinkage. Such gels swell more, dissolve more easily and increase in size more than high G content alginate gels. The gel strength also increases with increases in alginate concentration and with higher G content.

With reference to using $CaCl_2$ as a cross-linking reagent, concentrations up to about 0.2M may be used, for example from about 0.1M to 0.2M, such as about 0.1M.

One benefit associated with the use of alginates is that the gel's thermal uses are stable and independent of temperature (up to the boiling point of water). However, the kinetics of gelling can be modified by adjusting the prevailing temperature as might be necessary.

These factors, and others, may be manipulated to achieve the desired outcomes with respect to gel formation and gel properties. These kinds of factors will also need to be considered when using other types of cross-linkable and cross-linking reagents.

In certain embodiments of the present invention, the cross-linkable reagent may be a blend of an alginate and a pectin. Pectin is a biodegradable acidic carbohydrate polymer which is commonly found in plant cell walls. Pectin can consist of an α-(1→4)-linked polygalacturonic acid and rhamnose residue backbone that may be modified with neutral sugar side chains and non-sugar components such as methyl and acetyl groups. The extent of rhamnose insertions along the α-(1→4)-linked polygalacturonic acid backbone and other modifications vary depending on plant sources. The galacturonic acid content is generally more than 70% whereas the rhamnose content is typically <2%. Rhamnose residues are α-(1→2)-linked to galacturonic acid residues in the backbone. They cause the formation of a T-shaped kink in the backbone chain, and increases in rhamnose content lead to more flexible molecules. The neutral sugar side chains are attached to the rhamnose residues in the backbone at the O-3 or O-4 position. The rhamnose residues tend to cluster together on the backbone.

Methylation occurs at the carboxyl groups of galacturonic acid residues. The degree of methylation or methyl-esterification is defined as the percentage of carboxyl groups (galacturonic acid residues) esterified with methanol. Based on the degree of methylation or methyl-esterification, pectins are divided into two classes, low methoxyl pectin with a degree of methylation or methyl-esterification of <50% and a high methoxyl pectin with a degree of methylation or methyl-esterification of >50%.

Both high and low methoxyl form gels. However, these gels form via different mechanisms. High methoxyl pectin forms a gel in the presence of high concentrations of co-solutes (sucrose) at low pH. Low methoxyl pectin forms a gel in the presence of divalent cations such as $Ca^{2+}$, $Sr^{2+}$, $Zn^{2+}$, $Co^{2+}$ and $Ba^{2+}$, $Ca^{2+}$ ions in particular. The divalent cations-low methoxyl pectin gel network is built by formation of what is commonly referred to as an "egg-box" junction zone in which divalent cations cause the cross-linking of two stretches of polygalacturonic acid chains.

High methoxyl pectins are generally not reactive with divalent cations and therefore cannot form a divalent cation gel. However, certain high methoxyl pectins have been reported to be calcium sensitive and capable of calcium gel formation. In addition, high methoxyl pectins can be made calcium-reactive by a block wise de-esterification process while still having a degree of methylation or methyl-esterification of >50%.

Accordingly, low methoxyl pectins are generally preferred for embodiments of the present invention where a blend of alginate and pectin is used as the cross-linkable reagent. In this way, the same cross-linking reagent can be used for both the alginate and the pectin, when this combination is used. For example, the cross-linking reagent may be $CaCl_2$. Indeed, low methoxyl pectin may have a higher affinity for calcium, so the combination of low methoxyl pectin and alginate may lead to a cross-linked matrix with improved gel strength when compared to one of cross-linked alginate alone.

Calcium-low methoxyl pectin gel formation is influenced by several factors, including degree of methylation or methyl-esterification, ionic strength, pH, and molecular weight. The lower the degree of methylation or methyl-esterification and the higher the molecular weight, the more efficient the gelation. Furthermore, the calcium-low methoxyl pectin gelation is more efficient at a neutral pH of about 7.0 than about 3.5. Lastly, the addition of monovalent cations (e.g. the addition of NaCl to provide $Na^+$) enhances the gelation, i.e., less calcium is required for gel formation.

Low methoxyl pectins are typically obtained through a chemical de-esterification process. Commercial low methoxyl pectins typically have a degree of methylation or methyl-esterification of 20-50%. Completely de-esterified pectin can be referred to as "pectic acid" or "polygalacturonic acid". Pectic acid in the acid form is insoluble but is soluble in the salt form. The common salt form of pectic acid is either a sodium or potassium salt. Commercial pectins are mainly derived from citrus and apples. However, apart from citrus and apples, pectins can also be isolated from many other plants, such as aloe vera. Aloe vera leaves consist of two parts, an outer green rind and a clear inner gel which is also referred to as pulp. Aloe pectin is extracted from the inner gel or outer rind cell wall fibres. Use of a chelating agent at a slight alkaline pH has been found to be the most efficient extraction method. Aloe vera pectin is naturally a low methoxyl pectin, having a degree of methylation or methyl-esterification generally <30% that can be as low as <10%, and is capable of divalent cation gelation. A monovalent cation, such as $Na^+$, $K^+$ or $Li^+$ accelerates the formation of the gel. In addition, aloe vera pectin possesses several unique chemical properties that are particularly related to gelation. For example, it has a high molecular weight of >1×10$^6$ Da and a high intrinsic viscosity of >550 ml/g. Also, it has a high rhamnose content of >4%, which is at least twice the content of other pectins-derived from plants such as citrus, apple, sugar beet, and sunflower. Rhamnose is a key sugar in the pectin backbone and its content affects the flexibility of the molecule. Aloe vera pectin also possesses a rare sugar, 3-OMe-rhamnose which has not been described in any other pectins. The galacturonic acid content of aloe vera pectin is >70% and can be as high as >90%. Due to its characteristics, aloe vera pectin may be a preferred pectin for some embodiments of the present invention.

Other combinations of cross-linkable reagent and cross-linking reagent may be used in the present invention including: chitosan+tripolyphosphate, carboxymethylcellulose+Al$^{3+}$, k-carrageenan+K$^+$, k-carrageen+NH$_4^+$, pectin+Ca$^{2+}$, gelan gum+Ca$^{2+}$, and polyphosphazene+Ca$^{2+}$.

The cross-linkable reagent generally comprises a cross-linkable polymer, such as an alginate or a pectin, in a solution with solvent, such as water or an aqueous solution. Typically, the concentration of cross-linkable polymer in the solution will be from about 5% w/w to about 15% w/w, preferably from about 8% w/w to about 12% w/w, preferably about 10% w/w. The quantity of cross-linkable reagent used may be such that the concentration of cross-linkable polymer in the microparticle precursor composition may be from about 2% w/w to about 8% w/w, preferably from about 3% w/w to about 6% w/w, preferably from about 3% w/w to about 4% w/w. For example, in embodiments where the cross-linkable reagent is a blend of an alginate and a pectin, the concentration of sodium alginate in the microparticle precursor composition may be about 2% w/w and the concentration of pectin may also be about 2% w/w. In some other embodiments where the cross-linkable reagent is a blend of an alginate and a pectin, the concentration of sodium alginate in the microparticle precursor composition may be about 2% w/w and the concentration of pectin may be about 1% w/w. In some embodiments, the concentration of sodium alginate in the microparticle precursor composition may be about 2% w/w and the concentration of pectin may be between about 1% w/w and 2% w/w.

Cross-linked hydrogel matrices are often porous. The present invention provides a microparticle comprising a protective matrix to reduce microparticle porosity. By reducing microparticle porosity, it may be possible to prevent or to reduce exposure of a probiotic in the microparticle to the external environment, and to prevent or to reduce leakage of the probiotic from the microparticle.

In some embodiments, one or more other components of the microparticle precursor composition may be added to a component of the protective matrix precursor composition before all components of the protective matrix precursor have been blended together. As used herein, the protective matrix precursor composition encompasses blends that include any component of the microparticle, excluding the cross-linkable reagent and the cross-linking reagent. Thus, in some embodiments, the microparticle precursor composition can be considered to be a blend of the protective matrix precursor composition and the cross-linkable reagent.

The protective matrix provided by the present invention may mask flavours and/or prevent flavours from developing. Accordingly, in certain embodiments, the microparticle may mask any flavour of the probiotic or any other active in the microparticle, particularly when the flavour may be perceived by the consumer as being objectionable.

"Flavour" as used herein includes tastes or smells that may be perceived by the human or animal ingesting the microparticle. These flavours may be perceived by a consumer as being an objectionable flavour. An "objectionable flavour" as used herein includes tastes or smells that may be perceived by a consumer of the microparticle as being unpleasant or "off". These flavours may be astringent, bitter, musty, chalky, reminiscent or cardboard, fishy, sulfurous (i.e. a smell or taste associated with decomposing protein), metallic, rusty and/or generally foreign. Flavours may be inherent to one or more components of the protective matrix itself and/or of the microparticle, including any actives. Alternatively or additionally, flavours may result from one or more components of microparticle partially or fully degrading.

In some embodiments, the probiotic or another active in the microparticle may not have a flavour that is, of itself, considered objectionable. However, it may nevertheless be desirable to mask the flavour of this active as it may detract from the quality of a product that the microparticle may be incorporated into. For example, the microparticle may be incorporated into dietary supplements, functional foods and beverage products and in these goods it may be desirable for the flavour of the active not to taint the flavour of the good. As an example, if microparticles are incorporated into orange juice to provide a supplemented (fortified) juice, it may be desirable to mask the flavour of the active so that the consumer does not perceive any change in the flavour of the juice as a result of the supplementation (fortification).

For certain actives, in order to maximise absorption by human consumers, it can be desirable to transport the active(s) through the gastro-intestinal tract to the alkaline environment of the small intestine. For example, exposure to adverse conditions of the gastro-intestinal tract (e.g. exposure to gastric acid in the stomach) can compromise probiotic survival. Some actives can have an irritant effect on the stomach, so it is desirable encapsulate the active so that it is not available for absorption until it reaches the small intestine. Actives with an objectionable flavour such as fish oil, if released in the stomach, can cause the objectionable flavour to emanate up the oesophagus and/or provoke a gastric reflux response causing the flavour to be perceived by the consumer. This effect is sometimes known as food "repeating" on the consumer.

Components of the microparticle precursor composition may be selected so as to provide a microparticle with desirable active release characteristics. For example, microparticles may be produced in accordance with the present invention so as to have a matrix with enteric barrier properties. For example, in some embodiments, the cross-linkable reagent may be an alginate and alginate gels can exhibit enteric barrier properties. As described above, alginate gels show stability in low pH conditions so that active release is low, but swell rapidly and show dissolution and/or disintegration in weak alkaline conditions. This property enables alginate gels to be used effectively to deliver probiotics and other actives to the human small intestine. Accordingly, in some embodiments, the microparticle produced will be capable of passing through the acidic conditions of the stomach without any active(s) contained in the microparticle being released until the alkaline conditions of the small intestine are reached.

Cross-linked matrices produced from cross-linkable reagents such as alginates may be porous. The present invention relates to a protective matrix precursor composition comprising a blend of a denatured protein, a polyol plasticizer, trehalose and a carrier. As will be described in further detail below, the protective matrix formed by the precursor may compensate for the porosity of the cross-linked matrix formed by the cross-linkable reagent and the cross-linking reagent in order to prevent or to reduce ingress of degrading compounds, such as oxygen and/or moisture, and to prevent or to reduce leakage or diffusion of the active(s) from the microparticle. By doing so, the protective matrix may enhance, facilitate or complement the enteric barrier properties of the cross-linked matrix formed by the cross-linkable reagent and the cross-linking reagent. For example, the protective matrix may prevent degrading environmental factors, such as oxygen and moisture, from diffusing into the microparticle and compromising the microparticle during storage. Thus, the protective matrix may ensure that viable actives remain within the microparticle until such time as the microparticle is consumed and the enteric properties of the microparticle are utilised.

In some embodiments, the protective matrix prevents the flavour of the active(s) from emanating from microparticle in storage and the enteric barrier properties of the cross-linked matrix formed by the cross-linkable reagent and the cross-linking reagent prevents flavour emanation when the microparticle is within the stomach after consumption. In this way, the protective matrix may complement the enteric barrier properties of the cross-linked matrix.

In some embodiments, the combination of the protective matrix and cross-linked matrix may display greater stability in low pH conditions and as such greater stability when exposed to gastric acid than the cross-linked matrix alone. That is, the protective matrix may enhance the enteric barrier properties of the cross-linked matrix.

The protective matrix precursor composition of the present invention has three key ingredients: a polyol plasticizer, trehalose and a denatured protein, in a carrier. The carrier is a solvent for at least the trehalose. In general, the carrier will be miscible with the cross-linkable reagent. The carrier may be readily miscible with the solvent that is used, together with a cross-linkable polymer, to form the cross-linkable reagent. Typically, the carrier for will be water.

The protective matrix precursor composition may represent 5% to 20%, by weight, of the microparticle precursor composition. In some embodiments, the protective matrix precursor composition represents 7.5% to 13%, by weight, of the microparticle precursor composition. For example, the protective matrix precursor composition may be around 10%, by weight, of the microparticle precursor composition.

As used herein, the term "protein" refers to proteins having residues which are capable of undergoing thiol-disulfide interchange reactions and/or thiol oxidation reactions. In their natural states, proteins generally exist as either fibrous proteins or globular proteins. Fibrous proteins are water insoluble and serve as the main structural materials of animal tissues. Globular proteins are soluble in water or aqueous solutions of acids, bases or salts and feature widely in living systems. Fibrous proteins are typically fully extended and associated closely with each other in parallel structures, generally through hydrogen bonding, to form fibres. Globular proteins fold into complicated spherical structures held together by a combination of hydrogen, ionic, hydrophobic and covalent (disulfide) bonds. The chemical and physical properties of these proteins depend on the relative amounts of component amino acid residues and their placement along the protein polymer chain.

The protein may be a protein derived from nature or a synthetic polypeptide. In some embodiments, the protein may be a modified protein. For example, the protein may be one in which serine residues have been converted into cysteine residues using enzymic conversion.

The protein used of the present invention is preferably a globular protein. In embodiments where the protein is a fibrous protein, the fibrous protein is typically modified so that it becomes at water soluble. For example, where the fibrous protein is collagen it may be modified by hydrolysis to convert it into gelatine.

Preferred globular proteins are those which are isolated from milk, wheat, soy, egg, mung bean, pea, rice and corn. Proteins derived from milk include whey proteins and caseins. In certain embodiments, whey protein is the preferred protein for the protective matrix. Whey proteins are the proteins that remain soluble after caseins are precipitated at pH 4.6. Whey proteins, which are globular and heat labile in nature, consist of several component proteins, including α-Lactalbumin, β-Lactoglobulin, bovine serum albumin, immunoglobulins, and proteosepeptones.

In some embodiments, it may be desirable to select a protein from a plant source. For example, it may be desired to provide a microparticle that may be consumed by vegans.

In some embodiments, a protein with low allergenic properties may be selected for use in the protective matrix of the microparticle. For example, a pea or rice protein may be used as less people have allergic responses to these proteins in comparison to milk and soy proteins or wheat gluten. In addition, pea protein may be more readily digested than some other proteins.

The protein may be provided in the form of a protein concentrate or a protein isolate. A "protein concentrate" is a protein-rich product prepared by treating a protein source in an ultra-filtration process which removes liquid and smaller molecules. Often the ultra-filtration process used for preparing protein concentrates is a diafiltration process. Industrially produced protein concentrates, such as whey protein concentrate may have a protein content of 25 to 80%.

The term "protein isolate" as used herein refers to a product resulting from the extraction, subsequent concentration, and purification of proteinaceous material from a proteinaceous source. Protein isolates can be prepared by treating protein concentrates using, for example, an ion exchange process. Isolates may have protein contents in the order of 0.90%. In certain embodiments, the protein is a whey protein isolate.

The protein is typically provided in a solution or dispersion in a solvent. The protein may constitute about 5 to about 15% of the solution or dispersion by weight, preferably about 8 to about 12% by weight, more preferably about 10% by weight.

The solvent will often be the carrier, but it may be a component of the carrier when a mixture of liquids is used as the carrier. After forming the microparticle having the protective matrix, the solvent/carrier may be removed during syneresis of the gel. Water is often the preferred solvent/carrier.

Typically, the protein is denatured in the carrier in a ratio that will be used throughout the protective matrix precursor composition. That is, the total amount of carrier in the protective matrix precursor composition often comes from the dispersion or solution of the denatured protein in the carrier. Although, in some embodiments a portion of the carrier may be added at a later stage together with, or after, one or more of the other components is blended with the denatured protein. The quantities of other components of protective matrix precursor composition are typically determined on a weight basis in terms of the denatured protein and the total amount of carrier. For simplicity, the combination of the denatured protein and total amount of carrier are referred to herein as the denatured protein mixture even though in some embodiments a portion of the carrier may be added when, or after, one or more of the other components is blended with the denatured protein.

The denaturation process disrupts the quaternary, tertiary and secondary structures of the protein. The protein will be denatured in the presence of a solvent or the carrier so that the denatured protein can adopt a more extended structure as it is denatured. An extended protein conformation is advantageous for the production of a protective matrix in accordance with the present invention. Once extended, protein chains can associate through hydrogen, ionic, hydrophobic and covalent bonding. Protein chain interactions contribute to the cohesion of the protective matrix. In this regard, it is particularly desirable for the denaturation process to expose thiol-groups provided by cysteine and/or cystine residues to enable disulfide formation. Also, any hydrophobic groups provided by glycine, alanine, valine, leucine and isoleucine (i.e. those amino acids having aliphatic substituents) are also ideally exposed to permit hydrophobic bonding between protein chains. The hydrophobic groups are often located towards the centre of globular proteins in the natural state. Furthermore, the protein may include serine, threonine, asparagine and glutamine, which have hydrophilic substituents that are capable of forming hydrogen bonds.

In the present invention, the protein is denatured to expose thiol-groups of the protein and to enable disulfide formation. Disulfide formation refers to the formation of new —S—S— bonds which can occur either intermolecularly or intramolecularly. Disulfide formation can take place via thiol oxidation reactions in which the free sulfhydryl groups of cysteine residues become oxidized and form disulfide bonds. Additionally, thiol-disulfide exchange reactions can take place wherein existing intramolecular disulfide bonds can react with a thiol group thus forming a new disulfide bridge and releasing another free thiol group. For example, the whey protein β-lactoglobulin can be used in the present invention as this protein normally contains two pairs of cysteine residues that form disulfide bridges and one cysteine residue that contains a free thiol group.

The protein is denatured so as to sufficiently disrupt the quaternary, tertiary and secondary structures of the protein so that the thiol groups of the protein have the ability and conformational accessibility required to form disulfide bridges. Without being bound by theory, it is believed that the denatured protein molecules may cross-link to form aggregates distributed within the solvent/carrier.

The treatment whereby the thiol-disulfide exchange is effected can be a heat treatment, a chemical treatment or an enzymic treatment. In the present invention, the denaturation treatment is preferably a heat treatment. When a heat treatment is used, the protein solution or dispersion will be heated to a temperature above the denaturation temperature of the particular protein for a period of time sufficient to initiate disulfide cross-linkage reactions. The precise temperature and length of time for a given protein can be determined empirically. However, it is anticipated that the denaturation process will typically involve temperatures of from about 65° C. to 100° C., preferably from about 70° C. to 100° C., more preferably about 90° C. The duration of the heat treatment may be up to 3 hours, preferably from about 15 to 45 minutes, more preferably about 30 minutes.

Interactions between denatured protein chains are affected by the degree of chain extension and the nature and sequence of amino acid residues. In some embodiments, it may be desirable to use a mixture of proteins from different sources to optimize the protein chain interactions between the amino acid residues. For example, it can be desirable to produce a protective matrix using pea protein due to its hypoallergenic properties. However, pea protein has low amounts of cysteine, which may limit the ability of this protein to form disulfide cross-linkages. In contrast, rice protein has high levels of cysteine, which may lead to excessive cross-linkages resulting in a brittle protective matrix. In order to optimize the level to disulfide cross-linkages a combination of pea and rice protein may be used.

In order to improve the flexibility of the protective matrix, the protective matrix precursor composition of the present invention includes a polyol plasticizer. Polyols improve the flexibility of the protective matrix by hydrogen bonding with the denatured proteins, thereby increasing the intermolecular spacing between the protein chains. Suitable polyols plasticizers include polyalcohols such as glycerol, sorbitol and polyethylene glycol, as well as combinations thereof. Glycerol is a preferred plasticizer in certain embodiments.

Furthermore, as polyol plasticizers are generally kosmotropes, like trehalose, they contribute to the protective properties of the protective matrix. The polyol plasticizer will form hydrogen bonds with water in preference to the water/water hydrogen bonding. Accordingly, water in the microparticle becomes "destructured" and the formation of the ice crystal lattice is disrupted. In this way, the polyol plasticizer reduces the temperature at which ice crystals may form and, as a result, has cryoprotective properties for the probiotic. Thus, the polyol plasticizer contributes to improvements in probiotic survival following storage of the microparticle at low temperatures, for example following storage at −20° C.

The polyol plasticizer may be blended with the denatured protein mixture. Often the polyol plasticizer is blended with the denatured protein before trehalose is added. The polyol plasticizer may be added at a ratio of polyol plasticizer: denatured protein mixture of between about 30:70 to about 50:50, preferably about 35:65 to about 45:55, more preferably about 40:60, on a weight basis.

The protective matrix of the present invention further comprises, as an ingredient, trehalose. Trehalose is a bisacetal, non-reducing homodisaccharide in which two glucose units are linked together in a α-1,1-glycosidic linkage. The US Food and Drug Administration granted trehalose generally recognized as safe status in 2000. Trehalose stabilizes the denatured protein and improves the protective properties of the protective matrix.

As noted above, trehalose is a kosmotrope, thus the interaction between trehalose/water is much stronger than water/water interaction. Accordingly, trehalose causes "destructuring" of the water network and ordering the water molecules around itself (as a kosmotrope). Without being bound by theory, it is believed that, where water is the carrier and present in excess, trehalose does not interact directly with the denatured protein. Instead, water is excluded from around the protein and is ordered around trehalose. In accordance with this theory, the concentration of trehalose in the protective matrix may be selected such that there is competition between trehalose and the denatured protein, as well as the probiotic (and potentially any other active), for the available water. This competition causes water molecules to be destructured around the denatured protein and the probiotic and "structured" around trehalose. It is believed that trehalose manipulates the water structure around itself, such that the denatured protein and the probiotic are stabilized. Though the distribution of water molecules around trehalose will not be uniform, they may be oriented around trehalose in such a way that an ordered structure, with hydrogen bonds in all directions, is formed.

Furthermore, trehalose is believed to substitute carrier molecules, such as water, around the protein. By replacing carrier molecules with trehalose molecules that provide a hydrogen-bonding network, the three-dimensional structure of the denatured protein may be maintained as the microparticle containing the protective matrix dries and as the microparticle is subjected to other stresses, such as thermal stresses. This same mechanism may allow trehalose to protect certain actives, such as probiotics. Trehalose may have both cryoprotective and lyoprotective properties. In particular, the trehalose may enhance survival of the probiotic in cold storage at temperatures as low as −20° C.

With further reductions in carrier levels as the microparticle dries, the trehalose may further stabilize the denatured protein and other components of microparticle by immobilizing them inside a glassy sugar matrix. Trehalose can transit between one crystalline form and another, without relaxing its structural integrity, which is believed to facilitate formation of the protective glassy trehalose matrix around the other components of the microparticle, particularly the probiotic distributed within the matrix.

Formation of the glassy matrix is believed to enhance the oxygen, lipid and flavour barrier properties provided by the cross-linked denatured protein by preserving the three dimensional structure of the denatured protein and protecting it from abiotic stresses. In doing so, the trehalose may enable the denatured protein to better protect the probiotic in the microparticle and immobilize any diffusion of the probiotic or polyol plasticizer from the protective matrix. The trehalose may also enable the denatured protein to better protect any other active, such as a hydrophobic active, in the microparticle and immobilize it to prevent or suppress diffusion of it from the protective matrix.

By preventing or reducing diffusion of the polyol plasticizer from the protective matrix, the intermolecular spacing of the protein chains is maintained so that the matrix remains flexible even following syneresis of the gel produced following cross-linking of the cross-linkable reagent and the cross-linking reagent. Accordingly, the trehalose maintains the structure of the protective matrix so that it has long term stability and resilience. Also, as the trehalose has replaced carrier molecules around the protein chains, the intermolecular spacing may be closer to that of a solvated protein. Thus, trehalose can complement the polyol plasticizer to provide a flexible matrix.

Furthermore, the glassy matrix itself may inhibit the diffusion of oxygen, lipids or flavour compounds through the protective matrix. Therefore, the denatured protein and the trehalose can combine to form a dense matrix with good oxygen, lipid and flavour barrier properties. This dense matrix supports and protects the probiotic, and any other actives, distributed within the microparticle. Accordingly, the protective matrix may compensate for the porosity of the cross-linked matrix formed by the cross-linkable reagent and the cross-linking agent in order to prevent or to reduce ingress of degrading compounds, such as oxygen, and to prevent or to reduce leakage or diffusion of the active from the microparticle.

The glassy matrix comprises trehalose partly in an amorphous glassy phase and partly in a crystalline hydrate phase. The crystalline hydrate phase serves as an agent to dehydrate the amorphous phase, thereby enhancing the glass transition temperature of the amorphous glassy state. As used herein, the term glass or glassy state means a liquid phase of such high viscosity and low water content that all chemical reactions may be slowed to a near standstill. The advantage of the glassy matrix in achieving long term stability results from the fact that diffusion in glassy (vitrified) materials occurs at extremely low rates (e.g., microns/year). Trehalose has the highest glass transition temperature ($T_g$) of all the disaccharides. The optimal benefits of vitrification, that is immobilization of other components by the glassy matrix, for long-term storage are observed under conditions where $T_g$, is greater than the storage temperature. As trehalose has a high $T_g$, the protective matrix and the microparticle including the protective matrix may be stabilized over a wide range of storage temperatures.

In addition, despite trehalose's affinity for water, this disaccharide may enhance the microparticle's resilience to moisture. As noted above, trehalose has the highest $T_g$ of all the disaccharides. In general, the addition of water to an amorphous substance increases its mobility leading to a decrease in glass transition temperature ($T_g$). Though this anticipated decrease does occur in the case of trehalose, its $T_g$ is still much higher than that of other disaccharides such as sucrose or maltose. Accordingly, even though moisture may decrease $T_g$ it will typically remain higher than the storage temperature of the microparticle so that it will resist degradation.

Trehalose has a relative sweetness that is 45% that of sucrose and is effective at masking any flavours that may be associated with other components of the protective matrix or of the microparticle in general. For example, denatured proteins may have objectionable flavours. Proteins such as whey proteins often have a "cardboard" like taste, while rice proteins may have a chalky flavour. The objectionable flavour of the denatured protein may be effectively masked by the trehalose so that it is not perceived by the human or animal ingesting it.

It is envisioned that trehalose will effectively mask any objectionable flavour associated with the probiotic or any other active in the microparticle, or indeed any other component of the microparticle. Furthermore, any active, including the probiotic, in the microparticle may be effectively prevented from diffusing or leaking out of the microparticle, so any flavour compounds associated with the active should also be prevented from diffusing of leaking out of the microparticle.

Trehalose is typically added as the last ingredient to form the protective matrix precursor composition. However, it may be blended with the denatured protein mixture alone, or after one or more actives have been added. Trehalose may be added at a ratio of trehalose:denatured protein mixture of between about 40:60 to about 60:40, preferably about 45:55 to about 55:45, more preferably about 50:50, on a weight basis.

Once all components of the protective matrix precursor composition are blended together, the protective matrix precursor composition is typically sterilized. Depending upon the heat stability of the one or more actives to be distributed within the protective matrix, it may be desirable to sterilise the protective matrix precursor composition before blending it with any actives. For example, it will be appreciated that any sterilisation must be performed before the probiotic is blended with the protective matrix precursor composition due to the temperature sensitivity of the probiotic.

The protective matrix precursor composition may be sterilized by heating it to above 80° C. for a suitable length of time. For example, the protective matrix precursor composition may be sterilized at 85° C. for 30 minutes. The trehalose in the protective matrix precursor composition suppresses the formation of further disulfide cross-links between the denatured protein chains. Thus, the trehalose prevents the denatured protein from excessively cross-linking during the sterilizing process, as excessive cross-linking would lead to embrittlement of the protective matrix.

Typically, the sterilised protective matrix precursor composition is blended with the probiotic to form a probiotic-containing matrix precursor before blending the probiotic-containing matrix precursor with the cross-linkable reagent to form the microparticle precursor composition. This is done to ensure there is good contact between the protective matrix precursor composition and the probiotic so that the probiotic may be suitably distributed within, and protected by, the protective matrix in the ultimate microparticle.

Also, any other active is typically blended with protective matrix precursor composition before blending the resulting mixture with the cross-linkable reagent to form the microparticle precursor composition. As the protective matrix precursor composition is generally provided as an aqueous solution and as the cross-linkable reagent is generally provided in or as an aqueous solution, when the microparticle includes any hydrophobic actives, they will typically be immiscible in the protective matrix precursor composition and the cross-linkable reagent and it can be challenging to incorporate a hydrophobic active and a probiotic into a microparticle.

It can be undesirable to combine the hydrophobic active, probiotic, protective matrix precursor composition and, optionally, the cross-linkable reagent by emulsifying all these components together as the shear forces generated in emulsification processes may result in probiotic cell disruption and losses in probiotic viability.

In some embodiments where a hydrophobic active is used, the hydrophobic active may be blended with the denatured protein mixture, potentially without any additional emulsifier being used, to form an emulsion comprising the hydrophobic active. This emulsion may then be combined with the remaining components of the microparticle precursor composition.

Without being bound by theory, it is believed that the hydrophobic active may be blended with the denatured protein mixture to form a smooth and stable emulsion due to interactions between the hydrophobic active and hydrophobic groups of the protein, such as the aliphatic substituents of glycine, alanine, valine, leucine and isoleucine. That is, the combination of hydrophilic and hydrophobic groups in the protein enables it to act as an emulsifier to facilitate the blending of the hydrophobic active with the carrier, which is often water. Once again without being bound by theory, it is thought that aggregates of denatured protein and droplets of the hydrophobic active may form micelles, bilayer vesicles or bilayers that are structured so that the hydrophobic active is "shielded" from the solvent/carrier. These structures may be carried through into the microparticle. Thus, in the microparticle, the hydrophobic active may be partially or fully encapsulated within the denatured protein of the protective matrix.

Blending the hydrophobic active and the denatured protein, together with some or all of the carrier, prior to adding other components of the protective matrix precursor composition may enable the hydrophobic active and protein to interact more effectively in order to form the hydrophobic active "shielding" structure. This structure can then be stabilised through the addition of trehalose and the polyol plasticizer. However, it is not essential to combine the hydrophobic active with the protective matrix precursor composition in this manner.

Alternatively, to address the problem of incorporating the hydrophobic active into the microparticle without unduly compromising probiotic survival, some embodiments of the present invention provide a microparticle precursor composition comprising a blend of a probiotic, a cross-linkable reagent, a protective matrix precursor composition and an emulsion comprising a hydrophobic active. That is, prior to blending the hydrophobic active with other microparticle components, particularly the probiotic, the hydrophobic active is used to form an emulsion.

The emulsion comprising the hydrophobic active may be formed by combining the hydrophobic active with suitable liquid that is readily miscible with the protective matrix precursor composition and the cross-linkable reagent, but not readily miscible with the hydrophobic active. Typically, the hydrophobic active is emulsified with water using a suitable emulsifier, with this emulsion being readily miscible with the protective matrix precursor composition and the cross-linkable reagent being used. However, in some embodiments, the liquid may be the cross-linkable reagent.

The hydrophobic active and the liquid may be emulsified together using conventional emulsification techniques that will be known to those skilled in the art. In some embodiments, the emulsion may require further refining to achieve an emulsion in which the droplets of hydrophobic active are of a suitably small size. For example, multiple emulsification or homogenization steps may be required to refine the droplets of hydrophobic active to a suitably small size. A suitably small droplet size may facilitate a more even distribution of the hydrophobic active through the protective matrix of the microparticle. In some embodiments, the distribution of hydrophobic active droplets through the microparticle may be substantially uniform. Furthermore, with reductions in droplet size, the surface area to volume ratio of the hydrophobic active increases. Accordingly, there is more surface area available for the hydrophobic active to contact other components of the microparticle. The droplet size in the emulsion will also impact on the volume of interstitial space available between droplets. It is believed that the probiotic may advantageously be located within the interstitial spaces in some embodiments. A suitably small droplet size may be from 0.5 to 1 µm.

Certain hydrophobic actives, such as fish oil, are susceptible to oxidation. To prevent and/or delay onset of oxidation, the emulsion comprising the hydrophobic active may be formed in an inert atmosphere, such as a nitrogen or argon atmosphere, to reduce or prevent exposure to oxygen.

An emulsifier is used in order to enhance the stability of the emulsion comprising the hydrophobic active. As noted above, the emulsion may be formed with the denatured protein mixture, and an emulsifier in addition to the denatured protein may be used in those embodiments. The emulsifier may be any food-grade surface active ingredient, cationic surfactant, anionic surfactant and/or amphiphilic surfactant. Such emulsifiers can include one or more of, but are not limited to, lecithin, modified lecithin, chitosan, modified starches (e.g., octenylsuccinate anhydride starch), pectin, gums (e.g., locust bean gum, gum arabic, guar gum, etc.), alginic acids, alginates and derivatives thereof, cellulose and derivatives thereof, distilled monoglycerides, mono- and diglycerides, diacetyl tartaric acid esters of mono- and diglycerides (DATEM), polysorbate 60 or 80 (TWEEN 60 or 80), sodium stearyl lactylate, propylene glycol monostearate, succinylated mono- and diglycerides, acetylated mono- and diglycerides, propylene glycol mono- and diesters of fatty acids, polyglycerol esters of fatty acids, lactylic esters of fatty acids, glyceryl monosterate, propylene glycol monopalmitate, glycerol lactopalmitate and glycerol lactostearate, and mixtures thereof. In some embodiments, lecithin is used as an emulsifier.

The emulsifier may be added at a ratio of emulsifier:liquid of about 1:50 to about 1:15, preferably of about 1:45 to about 1:25. In some embodiments, the ratio used is about 1:29 on a weight basis. In some other embodiments, the ratio used is about 1:39.

Typically, the emulsifier is blended with at least a portion of the liquid before that emulsifier mixture is emulsified with the hydrophobic active. However, in some embodiments, the emulsifier, liquid and hydrophobic active may be mixed together simultaneously. In some embodiments, the emulsifier is mixed with the hydrophobic active prior to that mixture being emulsified with the liquid.

In some embodiments, the emulsifier is blended with around 20% to 50% (by weight), for example around one quarter or one third, of the liquid before that emulsifier mixture is mixed with the hydrophobic active and remaining liquid. The emulsifier may be added to the first portion of the liquid at a ratio of emulsifier:liquid portion of about 1:11 to about 1:7, preferably of about 1:10 to about 1:8, more preferably about 1:9 on a weight basis.

In view of the fact that the present invention relates to microparticles that are intended to be ingested by humans, in some embodiments, the mixture of emulsifier and liquid may be sterilised prior to emulsification with the hydrophobic active. The mixture of emulsifier and liquid may be sterilized by heating it to above 80° C. for a suitable length of time. For example, the mixture may be sterilized at 85° C. for 30 minutes. Often the sterilised mixture is cooled before emulsifying it with the hydrophobic active.

The hydrophobic active and mixture of emulsifier and liquid may be emulsified together at a ratio of hydrophobic active:mixture of emulsifier and liquid of from about 1:5 to about 5:1, preferably from about 10:35 to about 1:1, on a weight basis. In some embodiments, the ratio used is about 2:3 on a weight basis. In some other embodiments, the ratio used is about 1:3. In some embodiments, the ratio used is about 1:4.

Once the emulsion comprising the hydrophobic active is formed, the probiotic can be blended with the emulsion comprising the hydrophobic active to form a probiotic-containing emulsion. Typically, the probiotic is blended with the protective matrix precursor composition to form a probiotic-containing matrix precursor before blending with the emulsion comprising the hydrophobic active to form the probiotic-containing emulsion. In this way, the probiotic is well distributed through the protective matrix precursor composition and able to interact with it effectively. In particular, the probiotic may effectively interact with the trehalose.

The probiotic may be shear-sensitive in that subjecting the probiotic to high shear forces may result in cell disruption and losses in viability. In view of this, the probiotic should be blended with and dispersed though the any components of the microparticle in such a way that the viability of the probiotic is not unduly compromised. Accordingly, blending the probiotic with the emulsion comprising the hydrophobic active, or indeed any other component of the microparticle, involves subjecting the probiotic to suitably low shear blending. Suitably low shear blending is blending that is conducted below the shear rate at which significant cell disruption and losses in probiotic viability occur. For example, low shear rates may be the types of shear rates generated by a blending impeller operating at up to 300 rpm, such as from 100 to 300 rpm, but preferably 100 rpm or less. Low shear blending includes low shear mixing. Thus, in some embodiments, blending the probiotic with the emulsion comprising the hydrophobic active may comprise mixing the probiotic with the emulsion comprising the hydrophobic active.

The probiotic-containing emulsion can then be blended with the cross-linkable reagent to form the microparticle precursor composition. It will be appreciated that the blending with the cross-linkable reagent is also suitably low shear blending to ensure that the viability of the probiotic is not unduly compromised during formation of the microparticle precursor composition. Indeed, in the present invention, any probiotic-containing component that is used to produce the microparticle precursor composition, including any intermediate probiotic-containing mixtures, should be subjected to suitably low shear rates to ensure that the viability of the probiotic is not unduly compromised.

The hydrophobic active is typically the discontinuous phase in the emulsion comprising the hydrophobic active. By providing the hydrophobic active in the form of an emulsion with a liquid that is readily miscible with the cross-linkable reagent, the liquid carries the hydrophobic active and allows it to be effectively dispersed within the cross-linkable reagent. Thus, the discontinuous droplets of hydrophobic active are typically carried through into microparticle precursor composition. Furthermore, when the hydrophobic active is dispersed within the microparticle precursor composition, the microparticle produced using the precursor can have the hydrophobic active distributed within the cross-linked matrix.

Generally, for efficiency of mixing, the probiotic-containing matrix precursor is blended with the emulsion comprising the hydrophobic active before the blend comprising the probiotic and the hydrophobic active, i.e. the probiotic-containing emulsion, is blended with the cross-linkable reagent. In some embodiments, the probiotic cells may contact the emulsion droplets and become incorporated into them. This may enhance probiotic survival. Blending the hydrophobic active with the cross-linkable reagent before blending in the probiotic hampers the probiotic from effectively contacting the hydrophobic active.

The probiotic will generally be located in the continuous phase of the probiotic-containing emulsion. Likewise, the probiotic will typically be located in the continuous phase of the microparticle precursor composition. Most of the probiotic cells may be located in the interstitial spaces between the discontinuous hydrophobic active phase. The discontinuous droplets of hydrophobic active may be densely packed so that the interstitial spaces are shielded from the external environment. Without being bound by theory, it is believe that the probiotic is protected within the interstitial spaces so that its survival in the probiotic-containing emulsion and microparticle precursor composition is improved. Thus, it has been found that incorporating a hydrophobic active into a microparticle precursor composition in accordance with the present invention has a beneficial effect on probiotic survival during storage of the precursor composition, when compared to a microparticle precursor composition containing no hydrophobic active. For example, the microparticle precursor composition of the present invention may be stored ready for use at around 4° C. for two to three months with the probiotic survival being maintained at 90 to 98%.

Probiotic survival is calculated according to Formula 1 below.

$$\text{Probiotic Survival}(\%) = 100 \times \frac{\log_{10}\left(\begin{array}{c}\text{final number of } CFU \\ \text{per unit weight or unit volume}\end{array}\right)}{\log_{10}\left(\begin{array}{c}\text{initial number of } CFU \text{ per unit} \\ \text{weight or unit volume}\end{array}\right)} \quad \text{Formula 1}$$

The beneficial improvements in probiotic survival in the microparticle precursor composition may still be attained if the emulsion is formed using a lipid rather than a hydrophobic active. Accordingly, in another embodiment, the present invention provides a microparticle precursor composition comprising a blend of a probiotic, a protective matrix precursor composition (i.e. a blend of at least denatured protein, a polyol plasticizer, trehalose and a carrier), a cross-linkable reagent and an emulsion comprising a lipid. Suitable lipids may include those described above as being suitable for dissolving hydrophobic actives in order to put them into a form suitable for use in the present invention.

These embodiments of the present invention further provide a method of producing a microparticle precursor composition comprising: blending a probiotic with the protective matrix precursor composition to form a probiotic-containing matrix precursor; blending an emulsion comprising a lipid with the probiotic-containing matrix precursor to form a probiotic-containing emulsion; and blending the probiotic-containing emulsion with a cross-linkable reagent.

The present invention also provides a microparticle comprising a lipid and a probiotic distributed within a protective matrix.

The dispersed arrangement of the hydrophobic active (or lipid) and probiotic in the microparticle precursor composition may be carried through to the final microparticle. Thus, the hydrophobic active or lipid can be distributed within the protective matrix of the microparticle as a discontinuous phase. In some embodiments, the droplets of hydrophobic active or lipid are distributed through the matrix with a substantially uniform distribution. In some other embodiments, the distribution may lead to portions within protective matrix having a higher proportion of hydrophobic active or lipid than other portions.

Furthermore, the probiotic may be distributed within the cross-linked protective matrix of the microparticle so that it is located within the interstitial spaces between the hydrophobic active or lipid droplets. Accordingly, the probiotic may be protected within the interstitial spaces between the hydrophobic active or lipid droplets in the microparticle. The distribution of the probiotic within the protective matrix may be a substantially uniform distribution throughout the matrix.

Central to these embodiments of the invention is combining the hydrophobic active and the probiotic into the microparticle precursor composition in such a way that the viability of the probiotic is substantially maintained so that a microparticle with viable probiotic can be manufactured. These embodiments utilise an emulsion comprising a hydrophobic active in order to permit the hydrophobic active to be blended with the probiotic, protective matrix precursor composition and the cross-linkable reagent so as to form the microparticle precursor composition without subjecting the probiotic to stresses, namely shear forces, that will result in cell disruption and losses in viability.

Moreover, the present invention provides a shielding structure formed of droplets of hydrophobic active or of lipid that improves survival of the probiotic within the interstitial spaces between the droplets both in the microparticle precursor composition and the ultimate microparticle.

Blending the probiotic with the hydrophobic active as described above can improve probiotic survival during microparticle production. Improvement in probiotic survival is expressed as a percentage and calculated according to Formula 2 below.

$$\text{Improvement in Probiotic Survival }(\%) = 100 - \left(100 \times \frac{\log_{10}\left(\begin{array}{c}\text{number of } CFU \text{ per unit weight or} \\ \text{unit volume of the comparative product}\end{array}\right)}{\log_{10}\left(\begin{array}{c}\text{number of } CFU \text{ per unit weight or} \\ \text{unit volume of the product} \\ \text{of the present invention}\end{array}\right)}\right) \quad \text{Formula 2}$$

In some embodiments, the improvement in probiotic survival may be around 20% to around 50%, when compared to processes in which the hydrophobic active, probiotic and other microparticle components are emulsified together. For example, probiotic survival may be improved by around 30%.

Blending the emulsion comprising the hydrophobic active and the protective matrix precursor composition together may produce a blend in which aggregates of denatured protein, stabilised by trehalose and the polyol plasticizer surround the droplets of hydrophobic active from the emulsion comprising the hydrophobic active, thus shielding the hydrophobic active. By ensuring that the droplets of hydrophobic active are of a suitably small size, the aggregates of denatured protein, ultimately stabilised by trehalose and the polyol plasticizer, may more readily surround the hydrophobic active to form a "shielding" structure.

Insofar as the hydrophobic active of the composition is shielded by the denatured protein, the hydrophobic active benefits from the barrier properties of the protein. In particular, the denatured protein may act as a barrier to oxygen so as to limit or prevent oxidation of the hydrophobic active. In this way, the protective matrix may prevent or reduce flavours, particularly objectionable flavours, developing in the hydrophobic active.

As noted above, the protective matrix may prevent any active of the microparticle, including the probiotic, from diffusing or leaking out or significantly reduce or mitigate diffusion or leakage of the active. For example, when a microparticle has been added to a beverage, the protective matrix may prevent the active from diffusing or leaking out such that the relevant active does not become exposed to a degrading environment that would lead to the beneficial activity of the active being lost. The protective matrix may also prevent a degrading environment from developing within the microparticle itself. For example, the matrix may prevent or limit ingress of degrading compounds, such as oxygen, from the surrounding environment so as to prevent degradation of the relevant active within the microparticle. Thus, a degrading environment is one that may be within or external to the microparticle and involves exposing the relevant active to at least one degrading compound and/or degrading condition. Use of the protective matrix of the present invention may prevent or reduce exposure of the relevant active to a degrading environment.

Furthermore, the relevant active may be distributed within the protective matrix such that no flavour from the active is perceived by a human or animal ingesting the product due to the flavour masking activity of the trehalose in the protective matrix. In addition, the properties of the protective matrix may be such that individual flavour compounds that may be derived from the active are prevented or limited from diffusing or leaking through the microparticle.

The protective matrix may be particularly useful for protecting probiotics. The oxygen barrier properties of the protective matrix may promote survival of the probiotic. Also, the trehalose of the protective matrix may substitute water from around the probiotic and may form a glassy matrix at the bacterial cell membrane to stabilise the probiotic and protect it from environmental stresses that would otherwise compromise probiotic viability. Furthermore, the polyol plasticizer and the trehalose may combine synergistically to enhance survival of the probiotic.

In addition, probiotics may have flavours that might be considered objectionable by humans or animals ingesting them and the protective matrix may mask these flavours. The protective matrix may also prevent these flavours from emanating from the microparticle by preventing diffusion of the probiotic from the microparticle.

The protective matrix may prevent or reduce exposure of the probiotic, or any other active, to a degrading environment, which may result from active leakage or ingress of degrading compounds, for an extended period of time. Alternatively or additionally, diffusion or leakage of the probiotic (or any other active or a component of that active), may be prevented or limited such that no flavour from it is perceived by a human or animal ingesting the microparticle even after the microparticle has been stored for an extended period under suitable conditions. In some embodiments, the microparticle including the protective matrix may be stored without the probiotic, or any other active, losing its beneficial activity and/or without the flavour of the probiotic, or any other active, becoming perceivable for up to two months, preferably for up to four months, more preferably for up to six months, when suitable storage conditions are used. In some embodiments, the microparticle may be stored without the probiotic, or any other active, losing its beneficial activity and/or without the flavour of the probiotic, or any other active, becoming perceivable for up to two months, preferably for up to four months, more preferably for up to six months, when suitable storage conditions are used. Suitable storage conditions may include storing the microparticle at temperatures around −20° C. Suitable storage conditions may include vacuum packing the microparticle in foil.

In some embodiments, the microparticle may be added to another product, such as a beverage, to form a supplemented product. The protective matrix may prevent or reduce exposure of the probiotic, or any other active distributed within the protective matrix, to a degrading environment for the typical shelf life of the supplemented product. That is, the beneficial activity of the probiotic, or any other active, may be preserved for the entire shelf life of the supplemented product through the use of the protective matrix. Alternatively or additionally, diffusion or leakage of the probiotic, or any other active, may be prevented or limited such that no flavour from the probiotic, or the relevant other active, is perceived by a human or animal ingesting the supplemented product. Accordingly, in some embodiments, the shelf life of the product to be supplemented is not affected by the supplementation with the microparticle. The supplemented product may be stored at around 15° C. or below, preferably around 10° C. or below, more preferably 4° C. or below.

As an example, a microparticle in accordance with the present invention may be added to a beverage to form a beverage supplemented with a probiotic. The microparticle may have sufficient stability that the supplemented beverage may be stored for about four weeks, preferably for up to two months, more preferably for up to three months. For example, where the beverage is a fruit juice, such as a fresh fruit juice, the juice may be stored for around 4 weeks without the probiotic losing its beneficial activity and/or without the objectionable flavour of the probiotic becoming perceivable.

As noted above, certain actives may produce an objectionable flavour following degradation through exposure to, for example, oxygen. Thus, by preventing or limiting exposure to a degrading environment, the protective matrix of the present invention may be used to prevent objectionable flavours from developing.

The protective matrix of the present invention may be particularly suited to protecting actives that are susceptible to oxidative degradation, such as fish oil or other hydrophobic actives, which may be used in combination with the probiotic. These actives may inherently have an objectionable flavour. However, the flavour of these actives may become more objectionable if the active oxidizes. Therefore, the protective matrix may be advantageous for use in a microparticle containing an active susceptible to oxidative degradation as it may provide an effective oxygen barrier to prevent or suppress oxidation of the active. Where these active are lipids, such as fish oil, the trehalose of protective matrix may interact with the lipid to suppress or prevent oxidation. That is, trehalose may stabilize unsaturated bonds in the lipid against oxidation. As oxidation of the lipid can lead to the generation of volatile aldehydes that have objectionable flavours, suppressing oxidation of the lipid active prevents objectionable flavours from developing or reduces their development.

Other actives having objectionable flavours include vitamins B, which may have a bitter flavour. Vitamins B include Vitamin $B_1$ (thiamine), Vitamin $B_2$ (riboflavin). Vitamin $B_3$ (niacin or niacinamide), Vitamin $B_5$ (pantothenic acid), Vitamin $B_6$ (pyridoxine, pyridoxal, or pyridoxamine, or pyridoxine hydrochloride), Vitamin $B_7$ (biotin), Vitamin $B_9$ (folic acid) and Vitamin $B_{12}$ (various cobalamins, such as cyanocobalamin). The protective matrix of the present invention may be used to mask the flavour of one or more vitamins B that are distributed within the matrix.

In some embodiments, the denatured protein, polyol plasticizer and glassy trehalose matrix surrounds dispersed droplets of a liquid active. These droplets of active will have a lower tensile modulus compared to the denatured protein, polyol plasticizer and glassy trehalose matrix. Thus, the active may reduce the stiffness of the matrix and improve toughness.

In embodiments where a probiotic and a hydrophobic active are used, the glassy trehalose matrix may be concentrated in the interstitial spaces between the discontinuous hydrophobic active phase. Thus, the glassy trehalose matrix may reinforce the protection of the probiotic that may be provided by the hydrophobic active. In these embodiments, to facilitate formation of this structure the microparticle precursor composition may be produced by blending the probiotic with the protective matrix precursor composition before blending in the hydrophobic active.

Once the probiotic and the hydrophobic active have been blended with the protective matrix precursor composition, the cross-linkable reagent may be blended with these components to produce the microparticle precursor composition. In this way, the probiotic may be well embedded within the materials the will form the protective matrix, as a primary protective structure, and shielded within the interstitial spaces between hydrophobic active droplets, as a secondary protective structure, before it is blended with the cross-linkable reagent. The cross-linked matrix formed from the cross-linkable reagent and the cross-linking reagent will constitute a tertiary protective structure for the probiotic.

The components of the protective matrix precursor composition may stabilize the microparticle precursor composition it is blended into. Accordingly, a microparticle precursor composition in accordance with the present invention may have sufficient stability to allow it to be stored for extended periods without separating. For example, microparticle precursor compositions of the present invention may be stored ready for use for around two months, preferably around four months, more preferably up to six months. When a hydrophobic active is used, the trehalose may stabilize the interaction between the denatured protein and the hydrophobic active so that the active may be well dispersed throughout the carrier and the microparticle precursor composition remains a smooth and even emulsion. Thus, trehalose may facilitate the microparticle precursor composition of these embodiments having sufficient stability to allow it to be stored for extended periods, such as up to two or up to six months, without separating.

In some embodiments, the number of CFU of probiotic in a microparticle having the protective matrix may be maintained so that probiotic survival is 90% or more, for example around 99%, of the initial number of CFU after two months of storage under suitable conditions. In some embodiments, the number of CFU is maintained so that probiotic survival is 90% or more, for example around 99%, of the initial number of CFU after six months of storage under suitable conditions. Suitable storage conditions may include storing the microparticle at temperatures around −20° C. Suitable storage conditions may include vacuum packing the microparticle in foil.

In some embodiments, the viability of the probiotic in the microparticle is maintained such that the value of $\log_{10}$ (final number of CFU per unit weight or unit volume) is ≤1 less than the value of $\log_{10}$ (initial number of CFU per unit weight or unit volume), preferably the difference between the values is from 0 to 0.5, more preferably the difference is less than 0.02, even more preferably the difference is less than 0.004.

One or more components of the microparticle precursor composition may be susceptible to oxidization. Often oxidation susceptible components are actives, such as fish oil. To prevent or to reduce oxidation degradation of a susceptible component, which can lead to a loss of the beneficial activity associated with that component, certain steps of the method of producing the microparticle precursor composition may be conducted under an inert atmosphere, such as a nitrogen or argon atmosphere, to reduce or to prevent exposure to oxygen. In some embodiments, each and every step where the oxidation susceptible component or a mixture or blend containing the oxidation susceptible component is handled may be conducted under an inert atmosphere. Furthermore, in embodiments where the microparticle precursor composition contains an oxidation susceptible component, the microparticle may be produced under an inert atmosphere.

One or more components of the microparticle precursor composition may be susceptible to photodegradation. Similarly, to oxidation susceptible components, photodegradation susceptible components are often actives, such as fish oil. To prevent or to reduce photodegradation certain steps of the method of producing the microparticle precursor composition may be conducted in a darkened environment, such as a covered, opaque container, to reduce or to prevent exposure to light. In some embodiments, each and every step where the photodegradation susceptible component or a mixture or blend containing the photodegradation susceptible component is handled may be conducted in a darkened environment. In addition, in embodiments where the microparticle precursor composition contains a photodegradation susceptible component, the microparticle may be produced in a darkened environment.

One or more components of the microparticle precursor composition may be thermally sensitive and appropriate precautions can be taken during production of the microparticle precursor composition and the microparticle itself to avoid exposure to temperatures that will thermally degrade the relevant component.

The present invention provides a method of producing microparticles comprising providing the microparticle precursor composition in a finely divided state; and exposing the finely divided microparticle precursor composition to a cross-linking reagent to form microparticles. That is, the cross-linkable reagent of the microparticle precursor composition reacts with the cross-linking reagent so as to form a cross-linked matrix.

The cross-linked matrix provided by the cross-linkable reagent and cross-linking reagent will intermingle with the protective matrix which comprises cross-linked denatured protein. The intermingling may be such that the cross-linked matrix defines regions of protective matrix within the three dimensional network of the cross-linked matrix. That is, the cross-linked matrix may define the primary structure of the microparticle and the protective matrix is a secondary structure underpinning the cross-linked matrix.

There are a number of techniques, which will be known to those skilled in the art, that may be used to provide the microparticle precursor composition in a suitably finely divided state and expose it to the cross-linking agent. The microparticle precursor compositions are particularly suited being used to produce microparticles according to the method described in International Application No. PCT/AU2008/001695 (Publication No. WO 2009/062254), the entire contents of which are incorporated herein by reference. This method is the preferred method of producing microparticles in accordance with the present invention.

Other suitable methods of providing the microparticle precursor composition in a suitably finely divided state include air atomization in which the microparticle precursor composition is extruded through a syringe pump into an air atomizer device and sprayed into a cross-linking reagent bath. Electrostatic atomization (electrospray or electrohydrodynamic atomization (EHDA)), may also be suitable. In this technique, the microparticle precursor composition is supplied to a nozzle electrode and electrified to produce droplets. The droplets are dropped down into the cross-linking reagent. Spinning disk atomization, the Voretx-Bowl Disk Atomizer System, and micronozzle arrays may also be suitable for providing the microparticle precursor composition in a suitably divided state.

Once formed, the microparticles may be separated using known techniques and devices, including centrifugal separators, clarifiers, membrane filtration and filter presses depending upon the active, microparticle size and specific gravity. Depending upon the heat sensitivity of the probiotic, heat may be applied to cause syneresis of the gel in order to facilitate removal of carrier/solvent/liquid (typically water).

The microparticles may be in a form ready for use or may be added to another product as necessary. In some circumstances, trace reagents may need to be washed from the microparticles before they are used. For example, when $CaCl_2$ is used as the cross-linking reagent to effect gelling of an alginate (cross-linkable reagent), the microparticles may need to be washed to remove unused $CaCl_2$.

The microparticles may be spray dried, vacuum dried or freeze dried with or without the presence of other carrier solids (such as maltodextrins, sugars) as necessary to provide robustness. The cryoprotective properties of trehalose and the polyol plasticizer in the protective matrix may preserve the activity of the probiotic in the microparticle in the freeze drying process.

Microparticles formed using hydrogels may be porous, so it may be advantageous to apply a coating to the microparticle to improve its barrier properties. The microparticles of the present invention are particularly suited being coated using the coating composition described in Australian Provisional Patent Application No. 2012905167 and the coating composition described in an International patent application entitled "Coating composition" which claims priority from the aforementioned provisional application, and the contents these applications are hereby incorporated herein by reference. This coating composition is the preferred coating composition for microparticles in accordance with the present invention.

The microparticle may be coated using a variety of techniques. Suitable coating techniques include, but are not limited to, immersion coating, partial immersion coating, dipping, brushing, spin coating, flow coating and spray coating. For example, wet hydrogel microparticles may be partially immersed in a coating composition, mixed to ensure an even coating and then packaged.

The amount of coating composition used to coat a product may be equivalent to up to 50% of the weight of the microparticle to be coated. In some embodiments, the amount of coating used may be equivalent to 20 to 40% of the weight of the microparticle to be coated, preferably about 30% of the weight of the microparticle.

The microparticle may be stored at 4° C., preferably at −20° C. In some embodiments, it may be preferred to store microparticles by vacuum packing them in foil.

The following non-limiting examples illustrate embodiments of the present invention and some comparative examples.

Example 1

Whey Protein Isolates (WPI) Based Protective Matrix Precursor Composition

Preparing the WPI Mixture
Materials:
Whey protein isolates powder—10 g
Water—90 g
Method:
A 10% WPI solution was prepared by mixing together the WPI powder and water. The mixture was allowed to stand for 30 minutes after mixing so that the WPI could rehydrate. After standing, the 10% WPI solution was heat treated at 90° C. for 30 minutes. The resulting 10% WPI mixture was cooled before use.

Preparing the Protective Matrix Precursor Composition
Materials:
10% WPI Mixture as described above—60 g
Glycerol—40 g
Trehalose powder—30 g
Method:
The materials were blended together for 5 minutes at high speed using an IKA® T25 Digital ULTRA TURRAX® high-performance single-stage dispersing machine supplied by IKA-Works, Inc. The resulting composition was then sterilised at 85° C. for 30 minutes. The protective matrix precursor composition was cooled to room temperature before use.

Example 2

Fish Oil Emulsion

Preparing the Surfactant Mixture
Materials:
Lecithin—10 g
De-ionised Water—90 g
Method:
The surfactant mixture was prepared by dissolving lecithin in de-ionised water at ratio 1:9, using a mixer at a medium speed, until all lecithin was dissolved. The surfactant mixture was then sterilised at 90° C. for 30 minutes.

Preparing the Fish Oil Emulsion
Materials:
Surfactant Mixture as described above—100 g
Omega-3 Fish Oil—200 g
Water (Sterile)—200 g
Method:
1. The primary fish oil emulsion was prepared by weighing the components into a sterile container. The mixture was then homogenised with a Silverson Heavy Duty Laboratory mixer/emulsifier at medium speed for 5 minutes. The mixer was washed in absolute alcohol and sterile water before use. No oil droplets were visible on the surface of the emulsion.
2. The primary fish oil emulsion was passed through a two-stage Twin Panda 400 (GEA Niro Soavi) homogeniser (First Stage: 250 bars, Second Stage: 50 bars) twice to further reduce the emulsion droplet size to produce the final fish oil emulsion. The homogenisation equipment was cleaned with disinfectant and sterile water before each use.

Note:
To prevent and delay onset of fish oil oxidation, great care was taken when handling the fish oil and finished emulsion containing the omega-3 fish oil. Nitrogen gas was used to create a gas blanket to reduce oxygen exposure during preparation of the fish oil emulsion. The fish oil emulsion was also mixed in a container covered with foil to decrease light exposure.

Example 3

Cross-Linkable Reagent

Preparing the Cross-Linkable Reagent
Materials:
Sodium Alginate—20 g
Pectin—20 g
De-ionised Water—360 g Method:

The sodium alginate, pectin and de-ionised water were mixed together thoroughly. The cross-linkable reagent was then sterilised at 90° C. for 30 minutes the day before it was to be used.

Example 4

Microparticle Precursor Composition—*Lactobacillus casei* Lc431

Preparing the Microparticle Precursor Composition—*Lactobacillus casei* Lc431
Materials:
Protective Matrix Precursor Composition of Example 1—130 g
Frozen Concentrate of *Lactobacillus casei* Lc431—25 g
Fish Oil Emulsion of Example 2—500 mL
Cross-linkable Reagent of Example 3—400 g
Method:

The frozen concentrate of *Lactobacillus casei* Lc431 was melted in a sterile container at room temperature. Then, the microparticle precursor composition was prepared by combining the sterile, prepared compositions listed below in a sterile container in following order:
1. Protective Matrix Precursor Composition of Example 1
2. Melted Concentrate of *Lactobacillus casei* Lc431
3. Fish Oil Emulsion of Example 2
4. Cross-linkable Reagent of Example 3

The microparticle precursor composition was mixed together manually using a sterile spoon.
Note:

To prevent and delay onset of fish oil oxidation, great care was taken when handling the fish oil emulsion and microparticle precursor composition containing the omega-3 fish oil. Nitrogen gas was used to create a gas blanket to reduce oxygen exposure during preparation of the microparticle precursor composition. The microparticle precursor composition was also mixed in a container purged with nitrogen gas to decrease exposure to air (oxygen, in particular) and covered with foil to decrease exposure of the fish oil to light.

Example 5

Microparticle Precursor Composition—*Bifidobacterium lactis* BB12

Preparing the Microparticle Precursor Composition—*Bifidobacterium lactis* BB12
Materials:
Protective Matrix Precursor Composition of Example 1—130 g
Frozen Concentrate of Bifidobacterium *lactis* BB12—25 g
Fish Oil Emulsion of Example 2—500 mL
Cross-linkable Reagent of Example 3—400 g
Method:

The frozen concentrate of *Bifidobacterium lactis* BB12 was melted in a sterile container at room temperature. Then, the microparticle precursor composition was prepared by combining very well all the sterile, prepared compositions listed below in a sterile container in following order:
1. Protective Matrix Precursor Composition of Example 1
2. Melted Concentrate of *Bifidobacterium lactis* BB12
3. Fish Oil Emulsion of Example 2
4. Cross-linkable Reagent of Example 3

The microparticle precursor composition was mixed together manually using a sterile spoon.

Note:

To prevent and delay onset of fish oil oxidation, great care was taken when handling the fish oil emulsion and microparticle precursor composition containing the omega-3 fish oil. Nitrogen gas was used to create a gas blanket to reduce oxygen exposure during preparation of the microparticle precursor composition. The microparticle precursor composition was also mixed in a container purged with nitrogen gas to decrease exposure to air (oxygen, in particular) and covered with foil to decrease exposure of the fish oil to light.

Example 6

Microparticle Containing *Lactobacillus casei* Lc431

Producing the Microparticle
Materials:
Microparticle Precursor Composition of Example 4—~1 L
Cross-linking Reagent: 0.1M sterile calcium chloride solution (autoclaved at 121° C.)—~2 L
Method:

The following method is in accordance with the method described in International Application No. PCT/AU2008/001695 (Publication No. WO 2009/062254).
1. A pressure tank was filled with the microparticle precursor composition. Another pressure tank was filled with the cross-linking reagent.
2. Compressed nitrogen gas supplies were connected via appropriate connections to the pressure tanks. The exit tubing on each tank was not connected initially.
3. The pressure gauges were adjusted to the pre-determined pressure shown in Table 1 below and the valves were locked. The bottom nozzle liquid is for the cross-linking reagent and the top nozzle liquid is for the microparticle precursor composition.

TABLE 1

|  | Pressure (kPa) |
| --- | --- |
| Bottom nozzle nitrogen gas | 200 |
| Bottom nozzle liquid | 150 |
| Top nozzle nitrogen gas | 500 |
| Top nozzle liquid | 500 |

4. The liquid tubing of the cross-linking reagent pressure tank was connected to the reaction chamber and a cross-linking reagent mist was allowed to fill the reaction chamber for at least 2 minutes.
5. After 2 minutes, it was checked that the pressure in the microparticle precursor composition pressure tank is up to 500 kPa before connecting the liquid tubing of the pressure tank to the reaction chamber. An aerosol of the microparticle precursor composition was then produced and exposed to the cross-linking reagent mist.
6. The resulting microparticle slurry was collected from the collection tubing of the reaction chamber into a sterile container covered with foil.
7. After completion of the microparticle production, the pressure gauges were turned of and the apparatus was cleaned.
8. The microparticle slurry was filtered through a funnel layered with sterile Whatman filter paper (5C). The filtrate of wet microparticles was washed twice with sterile de-ionised water through the filter to wash out the calcium chloride residue.

Example 7

Microparticle Containing *Bifidobacterium lactis* BB12

Producing the Microparticle
Materials:
Microparticle Precursor Composition of Example 5—~1 L
Cross-linking Reagent: 0.1M sterile calcium chloride solution (autoclaved at 121° C.)—~2 L
Method:
The following method is in accordance with the method described in International Application No. PCT/AU2008/001695 (Publication No. WO 2009/062254).

1. A pressure tank was filled with the microparticle precursor composition. Another pressure tank was filled with the cross-linking reagent.
2. Compressed nitrogen gas supplies were connected via appropriate connections to the pressure tanks. The exit tubing on each tank was not connected initially.
3. The pressure gauges were adjusted to the pre-determined pressure shown in Table 2 below and the valves were locked. The bottom nozzle liquid is for the cross-linking reagent and the top nozzle liquid is for the microparticle precursor composition.

TABLE 2

|  | Pressure (kPa) |
| --- | --- |
| Bottom nozzle nitrogen gas | 200 |
| Bottom nozzle liquid | 150 |
| Top nozzle nitrogen gas | 500 |
| Top nozzle liquid | 500 |

4. The liquid tubing of the cross-linking reagent pressure tank was connected to the reaction chamber and a cross-linking reagent mist was allowed to fill the reaction chamber for at least 2 minutes.
5. After 2 minutes, it was checked that the pressure in the microparticle precursor composition pressure tank is up to 500 kPa before connecting the liquid tubing of the pressure tank to the reaction chamber. An aerosol of the microparticle precursor composition was then produced and exposed to the cross-linking reagent mist.
6. The resulting microparticle slurry was collected from the collection tubing of the reaction chamber into a sterile container covered with foil.
7. After completion of the microparticle production, the pressure gauges were turned of and the apparatus was cleaned.
8. The microparticle slurry was filtered through a funnel layered with sterile Whatman filter paper (5C). The filtrate of wet microparticles was washed twice with sterile de-ionised water through the filter to wash out the calcium chloride residue.

Example 8

Survival of *Bifidobacterium lactis* BB12 in the Microparticle

Microparticles prepared in accordance with Example 7 were added, while still wet, into milk for a study of *Bifidobactertium lactis* BB12 survival. The quantity of microparticles added to the milk was 0.5 g/100 mL and the milk was stored at 4° C. The probiotic loadings were measured as colony forming units per milliliter (CFU/mL).

The initial level of *Bifidobacterium lactis* BB12 was 8.46 $\log_{10}$ CFU/mL. After 7 days, the level reduced to 8.40 $\log_{10}$ CFU/mL, which corresponds to around 99% probiotic survival.

Example 9

Fish Oil Emulsion

Preparing the Surfactant Mixture
Materials:
Lecithin—10 g
De-ionised Water—90 g
Method:
The surfactant mixture was prepared by dissolving lecithin in de-ionised water at ratio 1:9, using a mixer at a medium speed, until all lecithin was dissolved. The surfactant mixture was then sterilised at 90° C. for 30 minutes.
Preparing the Fish Oil Emulsion
Materials:
Surfactant Mixture as described above—100 g
Omega-3 Fish Oil—100 g
Water (Sterile)—200 g
Method:

1. The primary fish oil emulsion was prepared by weighing the components into a sterile container. The mixture was then homogenised with a Silverson Heavy Duty Laboratory mixer/emulsifier at medium speed for 5 minutes. The mixer was washed in absolute alcohol and sterile water before use. No oil droplets were visible on the surface of the emulsion.
2. The primary fish oil emulsion was passed through a two-stage Twin Panda 400 (GEA Niro Soavi) homogeniser (First Stage: 250 bars, Second Stage: 50 bars) twice to further reduce the emulsion droplet size to produce the final fish oil emulsion. The homogenisation equipment was cleaned with disinfectant and sterile water before each use.

Note:
To prevent and delay onset of fish oil oxidation, great care was taken when handling the fish oil and finished emulsion containing the omega-3 fish oil. Nitrogen gas was used to create a gas blanket to reduce oxygen exposure during preparation of the fish oil emulsion. The fish oil emulsion was, also mixed in a container covered with foil to decrease light exposure.

Example 10

Cross-Linkable Reagent

Preparing the Cross-Linkable Reagent
Materials:
Sodium Alginate—20 g
Pectin—10 g
De-ionised Water—370 g
Method:
The sodium alginate, pectin and de-ionised water were mixed together thoroughly. The cross-linkable reagent was then sterilised at 90° C. for 30 minutes the day before it was to be used.

Example 10A

Cross-Linkable Reagent

Preparing the Cross-Linkable Reagent
Materials:
Sodium Alginate—20 g
Pectin—10 g
De-ionised Water—870 g Method:

The sodium alginate, pectin and de-ionised water were mixed together thoroughly. The cross-linkable reagent was then sterilised at 90° C. for 30 minutes the day before it was to be used.

Example 11

Microparticle Precursor Composition—*Lactobacillus casei* Lc431 and Fish Oil Containing Microparticles Preparing the Microparticle Precursor Composition—*Lactobacillus casei* Lc431 and Fish Oil
Materials:
Protective Matrix Precursor Composition of Example 1—75 g
Frozen Concentrate of *Lactobacillus casei* Lc431—25 g
Fish Oil Emulsion of Example 9—500 g
Cross-linkable Reagent of Example 10—400 g
Method:

The frozen concentrate of *Lactobacillus casei* Lc431 was melted in a sterile container at room temperature. Then, the microparticle precursor composition was prepared by combining the sterile, prepared compositions listed below in a sterile container in following order:
  1. Protective Matrix Precursor Composition of Example 1
  2. Melted Concentrate of *Lactobacillus casei* Lc431
  3. Fish Oil Emulsion of Example 9
  4. Cross-linkable Reagent of Example 10

The microparticle precursor composition was mixed together manually using a sterile spoon.
Note:

To prevent and delay onset of fish oil oxidation, great care was taken when handling the fish oil emulsion and microparticle precursor composition containing the omega-3 fish oil. Nitrogen gas was used to create a gas blanket to reduce oxygen exposure during preparation of the microparticle precursor composition. The microparticle precursor composition was also mixed in a container purged with nitrogen gas to decrease exposure to air (oxygen, in particular) and covered with foil to decrease exposure of the fish oil to light.

Example 12

*Lactobacillus casei* Lc431 and Fish Oil Containing Microparticles

Producing the Microparticle
Materials:
Microparticle Precursor Composition of Example 11—~1 kg
Cross-linking Reagent: 0.1M sterile calcium chloride solution (autoclaved at 121° C. for 15 minutes and cooled to room temperature)—~2 L
Method:

The following method is in accordance with the method described in International Application No. PCT/AU2008/001695 (Publication No. WO 2009/062254).
1. A pressure tank was filled with the microparticle precursor composition. Another pressure tank was filled with the cross-linking reagent.
2. Compressed nitrogen gas supplies were connected via appropriate connections to the pressure tanks. The exit tubing on each tank was not connected initially.
3. The pressure gauges were adjusted to the pre-determined pressure shown in Table 3 below and the valves were locked. The bottom nozzle liquid is for the cross-linking reagent and the top nozzle liquid is for the microparticle precursor composition.

TABLE 3

|  | Pressure (kPa) |
| --- | --- |
| Bottom nozzle nitrogen gas | 200 |
| Bottom nozzle liquid | 150 |
| Top nozzle nitrogen gas | 500 |
| Top nozzle liquid | 500 |

4. The liquid tubing of the cross-linking reagent pressure tank was connected to the reaction chamber and a cross-linking reagent mist was allowed to fill the reaction chamber for at least 2 minutes.
5. After 2 minutes, it was checked that the pressure in the microparticle precursor composition pressure tank is up to 500 kPa before connecting the liquid tubing of the pressure tank to the reaction chamber. An aerosol of the microparticle precursor composition was then produced and exposed to the cross-linking reagent mist.
6. The resulting microparticle slurry was collected from the collection tubing of the reaction chamber into a sterile container covered with foil.
7. After completion of the microparticle production, the pressure gauges were turned of and the apparatus was cleaned.
8. The microparticle slurry was filtered through a funnel layered with sterile Whatman filter paper (5C). The filtrate of wet microparticles was washed twice with sterile de-ionised water through the filter to wash out the calcium chloride residue.

Example 13

Microparticle Precursor Composition—*Lactobacillus casei* Lc431 Containing Microparticles Preparing the Microparticle Precursor Composition—*Lactobacillus casei* Lc431
Materials:
Protective Matrix Precursor Composition of Example 1—75 g
Frozen Concentrate of *Lactobacillus casei* Lc431—25 g
Cross-linkable Reagent of Example 10A—900 g
Method:

The frozen concentrate of *Lactobacillus casei* Lc431 was melted in a sterile container at room temperature. Then, the microparticle precursor composition was prepared by combining the sterile, prepared compositions listed below in a sterile container in following order:
  1. Protective Matrix Precursor Composition of Example 1
  2. Melted Concentrate of *Lactobacillus casei* Lc431
  3. Cross-linkable Reagent of Example 10A The microparticle precursor composition was mixed together manually using a sterile spoon.

Example 14

Lactobacillus casei Lc431 Containing Microparticles

Producing the Microparticle
Materials:
Microparticle Precursor Composition of Example 13—~1 kg
Cross-linking Reagent: 0.1M sterile calcium chloride solution (autoclaved at 121° C. for 15 minutes and cooled to room temperature)—~2 L
Method:
The following method is in accordance with the method described in International Application No. PCT/AU2008/001695 (Publication No. WO 2009/062254).
1. A pressure tank was filled with the microparticle precursor composition. Another pressure tank was filled with the cross-linking reagent.
2. Compressed nitrogen gas supplies were connected via appropriate connections to the pressure tanks. The exit tubing on each tank was not connected initially.
3. The pressure gauges were adjusted to the pre-determined pressure shown in Table 5 below and the valves were locked. The bottom nozzle liquid is for the cross-linking reagent and the top nozzle liquid is for the microparticle precursor composition.

TABLE 4

|  | Pressure (kPa) |
| --- | --- |
| Bottom nozzle nitrogen gas | 200 |
| Bottom nozzle liquid | 150 |
| Top nozzle nitrogen gas | 500 |
| Top nozzle liquid | 500 |

4. The liquid tubing of the cross-linking reagent pressure tank was connected to the reaction chamber and a cross-linking reagent mist was allowed to fill the reaction chamber for at least 2 minutes.
5. After 2 minutes, it was checked that the pressure in the microparticle precursor composition pressure tank is up to 500 kPa before connecting the liquid tubing of the pressure tank to the reaction chamber. An aerosol of the microparticle precursor composition was then produced and exposed to the cross-linking reagent mist.
6. The resulting microparticle slurry was collected from the collection tubing of the reaction chamber into a sterile container covered with foil.
7. After completion of the microparticle production, the pressure gauges were turned of and the apparatus was cleaned.
8. The microparticle slurry was filtered through a funnel layered with sterile Whatman filter paper (5C). The filtrate of wet microparticles was washed twice with sterile de-ionised water through the filter to wash out the calcium chloride residue.

Example 15

Liquid Sweet Formula Supplemented by Lactobacillus casei Lc431 and Fish Oil Containing Microparticles Microparticles were prepared in accordance with Example 12. These microparticles were then coated with a coating composition comprising a blend of denatured whey protein isolate, canola oil, glycerol, trehalose, and water. The microparticles were coated by manually mixing together microparticles and the coating composition at a microparticle:coating composition ratio of 10:3 on a weight basis.

The microparticles were added to a liquid sweet formula to produce a supplemented formula comprising, on a weight basis: 0.45% xanthan gum, 1.8% carrageenan gum, 2% fructose, 34% mango syrup and 13% microparticles, with the remainder being water. Once supplemented with the microparticles, the liquid sweet formula was packaged to produce 10 mL serving pouches. Each pouch contained 3 billion CFU of Lactobacillus casei Lc431 and 100 mg DHA/EPA due to the supplementation by the microparticles.

The pouches were stored initially at room temperature for two weeks and then at 4° C. The samples were tested over a six month period to assess probiotic survival and whether the flavour (i.e. smell/taste) of the Lactobacillus casei Lc431 and fish oil were perceptible. The results of these tests are shown below in Table 5 and in FIG. 1.

TABLE 5

Probiotic Viability and Flavour Perception Test Results.

| Measurement Date | Cell Viability ($Log_{10}CFU/mL$) | **Sensory Evaluation |
| --- | --- | --- |
| Week 2* | 7.85 | 0 |
| Week 3 | 7.7 | 0 |
| Week 4 | 7.26 | 0 |
| Week 5 | 7.68 | 0 |
| Week 6 | 7.17 | 0 |
| Week 7 | 7.58 | 0 |
| Week 8 | 7.38 | 0 |
| Week 9 | 7.38 | 0 |
| Week 10 | 7.05 | 0 |
| Week 11 | 7.16 | 0 |
| Week 12 | 7.15 | 0 |
| Month 6 | 6.50 | 0 |

NB:
*Stability test was started after 2 weeks storage at room temperature.
**Sensory evaluation rated from 0 = flavour (i.e. smell/taste) of the active(s) not detected to 10 = flavour of the active(s) detected very readily.

Example 16

Thin Base Drink Formula Supplemented by Lactobacillus casei Lc431 Containing Microparticles Microparticles were prepared in accordance with Example 14. These microparticles were then coated with a coating composition comprising a blend of denatured whey protein isolate, canola oil, glycerol, trehalose, and water. The microparticles were coated by manually mixing together microparticles and the coating composition at a microparticle:coating composition ratio of 10:3 on a weight basis.

The microparticles were added to a thin base drink formula to produce a supplemented formula comprising, on a weight basis: 3% Whey Protein Isolate, 2% Litess II from DuPont™ Danisco®, 1% Prebiotic Hi-Maize® from National Starch, 4% trehalose, 0.75% stevia, 0.05% xanthan gum, 0.1% potassium sorbate and 2% microparticles, with the remainder being water.

Figure 2:
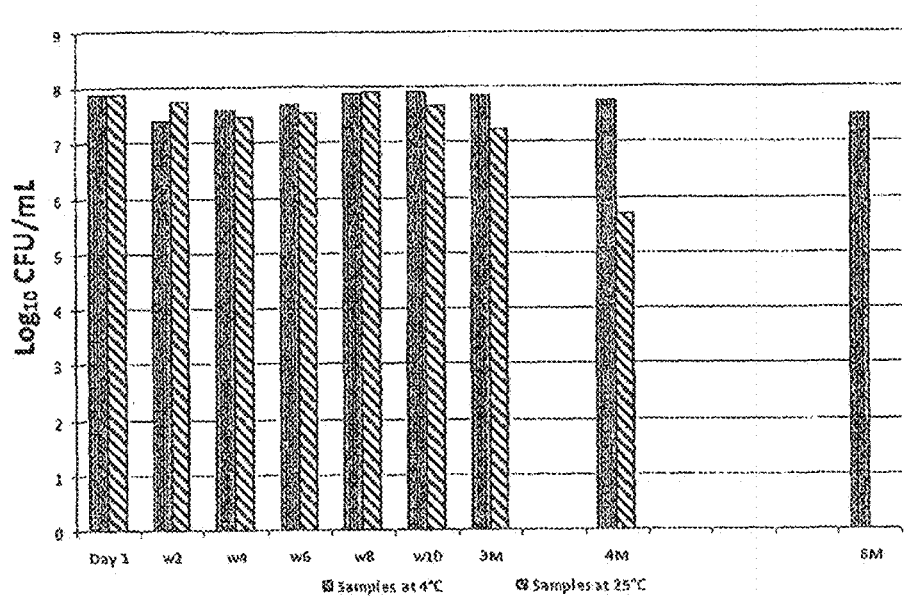
FIG. 2 shows the results of probiotic survival tests described in Example 16.

Samples of the supplemented thin base drink formula were stored at either 4° C. or 25° C. and tested over a six month period to assess probiotic survival. The results of these tests are shown below in Table 6 and in FIG. 2.

TABLE 6

Probiotic Viability Test Results.

| Measurement Date | Cell Viability for Samples Stored at 4° C. ($Log_{10}$CFU/mL) | Cell Viability for Samples Stored at 25° C. s ($Log_{10}$CFU/mL) |
|---|---|---|
| Day 1 | 7.87 | 7.87 |
| Week 2 | 7.4 | 7.75 |
| Week 4 | 7.6 | 7.45 |
| Week 6 | 7.67 | 7.52 |
| Week 8 | 7.89 | 7.90 |
| Week 10 | 7.90 | 7.65 |
| Week 12 | 7.87 | 7.25 |
| Month 4 | 7.75 | 5.7 |
| Month 6 | 7.50 | |

Example 17

Thin Base Drink Formula Supplemented by *Lactobacillus casei* Lc431 and Fish Oil Containing Microparticles Microparticles were prepared in accordance with Example 12. These microparticles were then coated with a coating composition comprising a blend of denatured whey protein isolate, canola oil, glycerol, trehalose, and water. The microparticles were coated by manually mixing together microparticles and the coating composition at a microparticle:coating composition ratio of 10:3 on a weight basis.

The microparticles were added to a thin base drink formula to produce a supplemented formula comprising, on a weight basis: 3% Whey Protein Isolate, 2% Litess II from DuPont™ Danisco®, 1% Prebiotic Hi-Maize® from National Starch, 4% trehalose, 0.75% *stevia*, 0.05% xanthan gum, 0.1% potassium sorbate and 2% microparticles, with the remainder being water.

Figure 3:
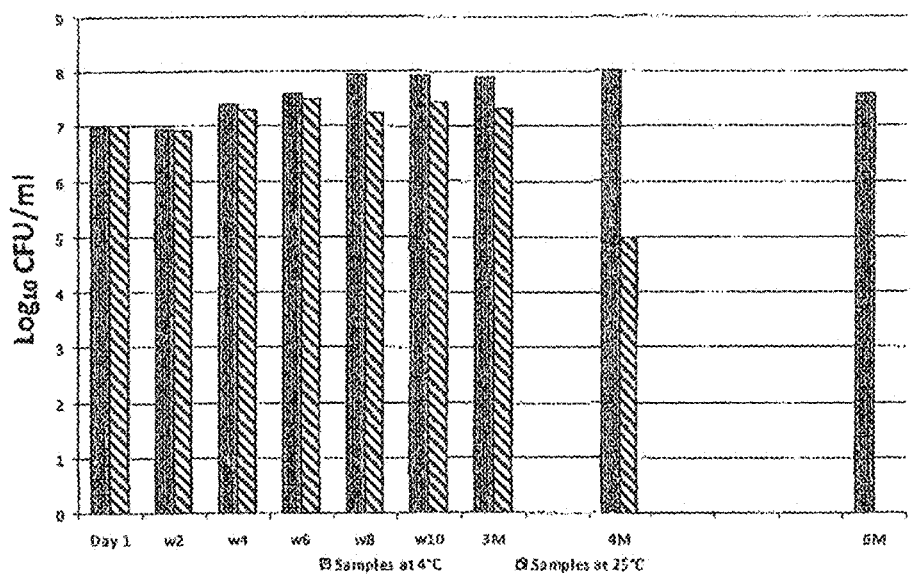
FIG. 3 shows the results of probiotic survival tests described in Example 17.

Samples of the supplemented thin base drink formula were stored at either 4° C. or 25° C. and tested over a six month period to assess probiotic survival. The results of these tests are shown below in Table 7 and FIG. 3.

TABLE 7

Probiotic Viability Test Results.

| Measurement Date | Cell Viability for Samples Stored at 4° C. ($Log_{10}$CFU/mL) | Cell Viability for Samples Stored at 25° C. ($Log_{10}$CFU/mL) |
|---|---|---|
| Day 1 | 7.00 | 7.00 |
| Week 2 | 6.95 | 6.92 |
| Week 4 | 7.39 | 7.33 |
| Week 6 | 7.61 | 7.50 |
| Week 8 | 7.95 | 7.24 |
| Week 10 | 7.94 | 7.44 |
| Week 12 | 7.92 | 7.33 |
| Month 4 | 8.04 | 5.00 |
| Month 6 | 7.61 | |

Example 18

Meal Replacement Protein Powder Supplemented by *Lactobacillus casei* Lc431 Containing Microparticles Microparticles were prepared in accordance with Example 14. These microparticles were then coated with a coating composition comprising a blend of denatured whey protein isolate, canola oil, glycerol, trehalose, and water. The microparticles were coated by manually mixing together microparticles and the coating composition at a microparticle:coating composition ratio of 10:3 on a weight basis.

The microparticles were added to a commercially available meal replacement protein powder at a 1:49 ratio, by weight.

Figure 4:
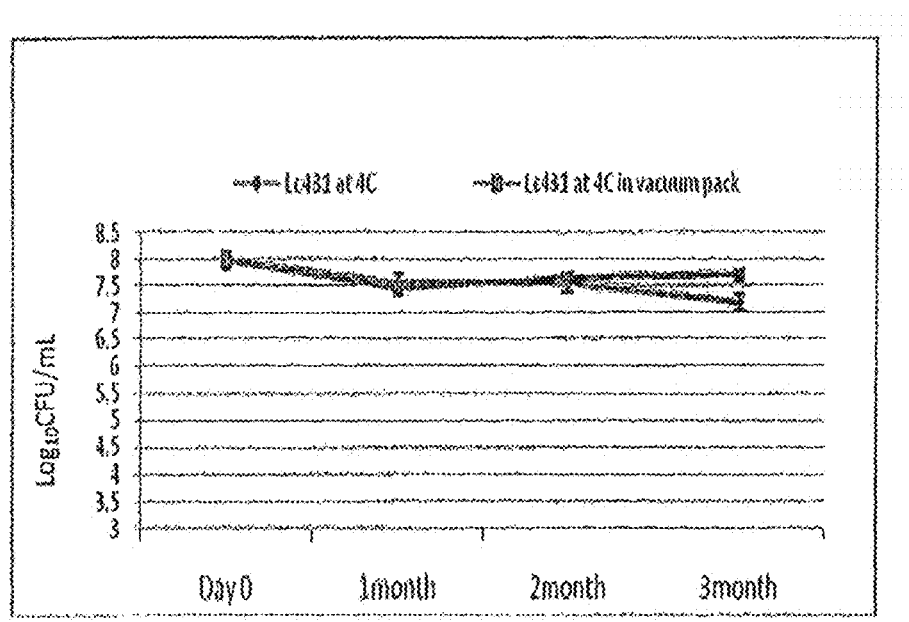
FIG. 4 shows the results of probiotic survival tests described in Example 18.

Samples of the supplemented meal replacement protein powder were stored in either a sealed container or vacuum packed in foil. These samples were stored at 4° C. and tested over a three month period to assess probiotic survival. The results of these tests are shown below in Table 8 and FIG. 4.

TABLE 8

Probiotic Viability Test Results.

| Sample | Cell Viability after 0 Days of Storage at 4° C. ($Log_{10}$CFU/mL) | Cell Viability after 1 Month of Storage at 4° C. ($Log_{10}$CFU/mL) | Cell Viability after 2 Months of Storage at 4° C. ($Log_{10}$CFU/mL) | Cell Viability after 3 Months of Storage at 4° C. ($Log_{10}$CFU/mL) |
|---|---|---|---|---|
| Dry blend in container | 8.01 | 7.57 | 7.58 | 7.22 |
| Dry blend in vacuum foil pack | 8.01 | 7.47 | 7.67 | 7.73 |

Example 19

Beverages Supplemented by *Lactobacillus casei* Lc431 Containing Microparticles—Stability of Encapsulation at Low pH Microparticles were prepared in accordance with Example 14. These microparticles were then coated with a coating composition comprising a blend of denatured whey protein isolate, canola oil, glycerol, trehalose, and water. The microparticles were coated by manually mixing together microparticles and the coating composition at a microparticle:coating composition ratio of 10:3 on a weight basis.

Part 1—Addition to a Juice-Based Beverage

Microparticles were added to juice drink comprising, by weight, 20% apple juice, 5% mango juice and 75% water to produce a supplemented juice drink comprising 1% microparticles on a weight basis. The supplemented juice was pH 3.6.

Figure 5:
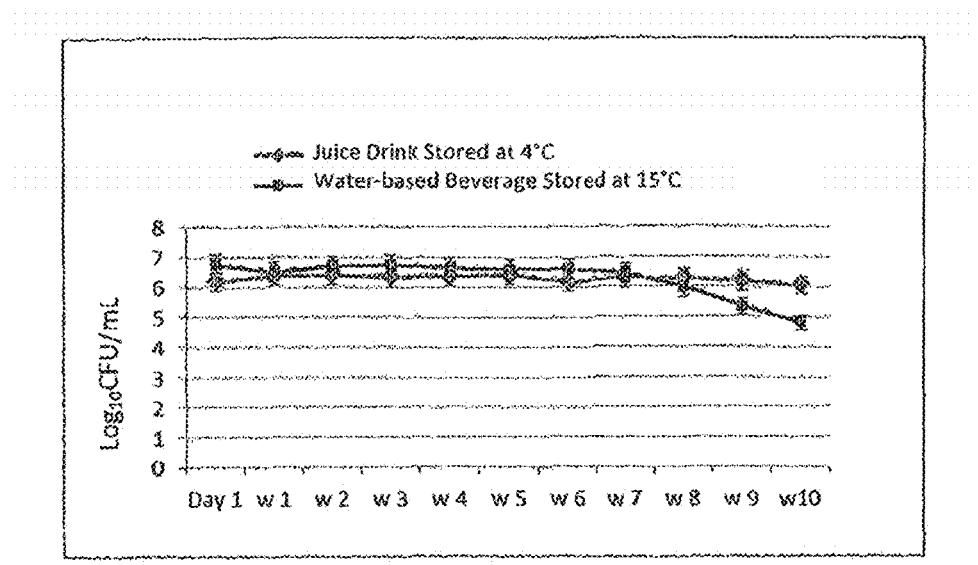
FIG. 5 shows the results of probiotic survival tests described in Example 19.

Samples of the supplemented juice drink were stored at 4° C. and tested over a ten week period to assess probiotic survival. The results of these tests are shown below in Table 9 and FIG. 5.

Part 2—Addition to a Water-Based Beverage

Microparticles were added to water-based beverage to produce a supplemented beverage comprising, on a weight basis: 4% trehalose, 2% Litess II from DuPont™ Danisco®, 2% fructose, 0.2% xanthan gum, 0.05% potassium sorbate, 0.025% ascorbic acid, 1% microparticles. The supplemented beverage was pH 4.5.

Samples of the supplemented beverage were stored at 15° C. and tested over a ten week period to assess probiotic survival. The results of these tests are shown below in Table 9 and FIG. 5.

TABLE 9

Probiotic Viability Test Results.

| | Cell Viability (Log$_{10}$CFU/mL) | |
|---|---|---|
| Measurement Date | Samples of Juice Drink Stored at 4° C. | Samples of Water-based Beverage Stored at 15° C. |
| Day 1 | 6.2 | 6.77 |
| Week 1 | 6.4 | 6.54 |
| Week 2 | 6.43 | 6.73 |
| Week 3 | 6.34 | 6.74 |
| Week 4 | 6.37 | 6.65 |
| Week 5 | 6.40 | 6.60 |
| Week 6 | 6.18 | 6.62 |
| Week 7 | 6.34 | 6.50 |
| Week 8 | 6.30 | 6.01 |
| Week 9 | 6.22 | 5.37 |
| Week 10 | 6.07 | 4.82 |

Example 20

Stability of *Lactobacillus casei* Lc431 Containing Microparticles at a High Storage Temperature Microparticles were prepared in accordance with Example 14. These microparticles were then coated with a coating composition comprising a blend of denatured whey protein isolate, canola oil, glycerol, trehalose, and water. The microparticles were coated by manually mixing together microparticles and the coating composition at a microparticle:coating composition ratio of 10:3 on a weight basis.

The microparticles were combined into the following blends.

Blend 1: microparticles and PromOat™ blended together at a ratio, by weight, of 1:9.

Blend 2: microparticles, Hi-Maize® Resistant Starch and inulin blended together at a ratio, by weight, of 1:5:4.

Blend 3: microparticles, Hi-Maize® Resistant Starch and trehalose blended together at a ratio, by weight, of 1:5:4.

For the purposes of comparison, comparative blends were prepared as follows:

Frozen *Lacrobacillus casei* Lc431 concentrate was thawed to liquid and centrifuged at 4000 rpm for 5 minutes to obtain the cell mass. This cell mass was used to prepare the following comparative blends.

Comparative Blend 1: *Lactobacillus casei* Lc431 concentrate (i.e. un-encapsulated probiotic) and PromOat™ blended together at a ratio, by weight, of 1:9.

Comparative Blend 2: *Lactobacillus casei* Lc431 concentrate (i.e. un-encapsulated probiotic), Hi-Maize® Resistant Starch and inulin blended together at a ratio, by weight, of 1:5:4.

Comparative Blend 3: *Lactobacillus casei* Lc431 concentrate (i.e. un-encapsulated probiotic), Hi-Maize® Resistant Starch and trehalose blended together at a ratio, by weight, of 1:5:4.

Blends 1, 2 and 3 and Comparative Blends 1, 2 and 3 were stored at 37° C. for one week and tested to assess probiotic survival following storage. The results of these tests are shown below in Table 10.

TABLE 10

Probiotic Viability Test Results.

| | Cell Viability (Log$_{10}$CFU/mL) | |
|---|---|---|
| Sample | Day 0 | Week 1 |
| Blend 1 | 8.26 | 8.72 |
| Comparative Blend 1 | 9.48 | 5 |
| Blend 2 | 8.09 | 7.67 |
| Comparative Blend 2 | 9.35 | 5 |
| Blend 3 | 8.18 | 7.54 |
| Comparative Blend 3 | 9.00 | 5 |

Example 21

Survival of *Lactobacillus* Case Lc431 Following Storage—*Lactobacillus casei* Lc431 and Fish Oil Containing Microparticles Microparticles were prepared in accordance with Example 12. These microparticles were then coated with a coating composition comprising a blend of denatured whey protein isolate, canola oil, glycerol, trehalose, and water. The microparticles were coated by manually mixing together microparticles and the coating composition at a microparticle:coating composition ratio of 10:3 on a weight basis.

Samples of the wet microparticles were stored in a sealed container (i.e a container with a tight lid) at either 4° C. or −20° C. for a study of *Lactobacillus casei* Lc431 survival. The probiotic viability measurements taken from samples stored at 4° C. over a 3 month period are shown below in Table 11, while the probiotic viability measurements taken from samples stored at −20° C. over a four month period are shown below in Table 12.

TABLE 11

Probiotic Viability Test Results for Samples Stored at 4° C.

| Measurement Date | Batch 160812 Cell Viability (Log$_{10}$ CFU/g) | Batch 060912 Cell viability (Log$_{10}$ CFU/g) | Batch 111112 Cell viability (Log$_{10}$ CFU/g) |
|---|---|---|---|
| Day 0 | 9.75 | 9.92 | 9.95 |
| 1 month | 9.78 | 9.73 | n/a |
| 2 month | 9.74 | 9.78 | 9.48 |
| 3 month | 9.4 | 8.78 | 7.45 |

TABLE 12

Probiotic Viability Test Results for Samples Stored at −20° C.

| Measurement Date | Batch 160812 Cell Viability (Log$_{10}$ CFU/g) | Batch 060912 Cell viability (Log$_{10}$ CFU/g) | Batch 111112 Cell viability (Log$_{10}$ CFU/g) |
|---|---|---|---|
| Day 0 | 9.75 | 9.92 | 9.95 |
| 1 month | n/a | n/a | n/a |
| 2 month | 9.79 | 9.87 | 9.18 |
| 3 month | 9.62 | 9.62 | 9.18 |
| 4 month | 9.34 | 9.58 | n/a |

Example 22

Meal Replacement Protein Powder Supplemented by *Lactobacillus casei* Lc431 Containing Microparticles Microparticles were prepared in accordance with Example 14. These microparticles were then coated with a coating composition comprising a blend of denatured whey protein isolate, canola oil, glycerol, trehalose, and water. The microparticles were coated by manually mixing together microparticles and the coating composition at a microparticle:coating composition ratio of 10:3 on a weight basis.

The microparticles were added to a commercially available meal replacement protein powder at a 1:49 ratio, by weight.

Samples of the supplemented meal replacement protein powder were vacuum packed in foil stored at either 4° C. or 25° C. and tested over a twelve week period to assess probiotic survival. The results of these tests are shown below in Table 13.

TABLE 13

Probiotic Viability Test Results

| Measurement Date | Cell viability ($Log_{10}$ CFU/g) for samples stored at 4° C. | Cell viability ($Log_{10}$ CFU/g) for samples stored at 25° C. |
| --- | --- | --- |
| Day 0 | 7.99 | 7.99 |
| Week 2 | 7.43 | 7.10 |
| Week 4 | 7.57 | 6.67 |
| Week 8 | 7.70 | n/a |
| Week 12 | 7.85 | n/a |

Example 23

Flour-based Powder Supplemented by *Lactobacillus casei* Lc431 Containing Microparticles Microparticles were prepared in accordance with Example 14. These microparticles were then coated with a coating composition comprising a blend of denatured whey protein isolate, canola oil, glycerol, trehalose, and water. The microparticles were coated by manually mixing together microparticles and the coating composition at a microparticle:coating composition ratio of 10:3 on a weight basis.

The microparticles were blended with rice flour and trehalose at a microparticle:rice flour:trehalose ratio of 1:5:4, by weight, to form a supplemented flour-based powder.

Samples of the supplemented flour-based powder were stored in a sealed container (i.e a container with a tight lid) at 37° C. and tested over a two week period to assess probiotic survival. The results of these tests are shown below in Table 14.

TABLE 14

Probiotic Viability Test Results

| Measurement Date | Cell viability ($Log_{10}$ CFU/g) for samples stored at 37° C. |
| --- | --- |
| Day 0 | 8.52 |
| Week 1 | 8.62 |
| Week 2 | 7.01 |

Comparative Example 1

Survival of *Bifidobacterium lactis* BB12 in a Comparative Microparticle

Microparticles containing *Bifidobacterium lactis* BB12 and trehalose were prepared in accordance with Example 7. However, the Microparticle Precursor Composition used to prepare the microparticles for this Comparative Example had the following composition, for 400 g of composition: 200 g of melted concentrate of *Bifidobacterium lactis* BB12, 5% trehalose, 1% lecithin, 2% sodium alginate and 0.2% TWEEN 80, with the remainder of the composition being water.

These microparticles were freeze-dried and then added into milk for a study of *Bifidobacterium lactis* BB12 survival. The quantity of microparticles added to the milk was 30 mg/300 mL and the milk was stored at 4° C. The probiotic loadings were measured as colony forming units per milliliter (CFU/mL).

The initial level of *Bifidobacterium lactis* BB12 was 7.35 $log_{10}$ CFU/mL. After 7 days, the level reduced to 6.96 $log_{10}$ CFU/mL, which corresponds to around 94.7% probiotic survival.

Comparative Example 2

Survival of *Bifidobacterium lactis* BB12 in a Comparative Microparticle

Microparticles containing *Bifidobacterium lactis* BB12 and trehalose were prepared in accordance with Example 7. However, the Microparticle Precursor Composition used to prepare the microparticles for this Comparative Example had the following composition, for 400 g of composition: 200 g of melted concentrate of *Bifidobacterium lactis* BB12, 5% trehalose, 1% lecithin, 2% sodium alginate and 0.2% TWEEN 80, with the remainder of the composition being water.

The wet microparticles were then mixed with trehalose and WPI power in accordance with the following ratio on a weight basis: (wet microparticles:trehalose:WPI powder) 80:20:20. The microparticles were then vacuum dried at 40° C. for 24 hours prior to a study of *Bifidobacterium lactis* BB12 survival. The probiotic loadings are measured as colony forming units per gram (CFU/g).

The initial level of *Bifidobacterium lactis* BB12 after vacuum drying was 10.46 $log_{10}$ CFU/g. After 5 days of storage at 4° C., the level reduced to 10.36 $log_{10}$ CFU/g, which corresponds to around 99% probiotic survival.

Comparative Example 3

Survival of *Bifidobacterium lactis* BB12 in a Comparative Microparticle

Microparticles containing *Bifidobacterium lactis* BB12 and trehalose were prepared in accordance with Example 7.

However, the Microparticle Precursor Composition used to prepare the microparticles for this Comparative Example had the following composition, for 400 g of composition: 200 g of melted concentrate of Bifidobacterium lactis BB12, 5% trehalose, 1% lecithin, 2% sodium alginate and 0.2% TWEEN 80, with the remainder of the composition being water.

The wet microparticles were then mixed with trehalose and Hi-Maize® Resistant Starch in accordance with the following ratio on a weight basis: (wet microparticles: trehalose:Hi-Maize® Resistant Starch) 80:20:20. The microparticles were then vacuum dried at 40° C. for 24 hours prior to a study of Bifidobacterium lactis BB12 survival. The probiotic loadings are measured as colony forming units per gram (CFU/g).

The initial level of Bifidobacterium lactis BB12 after vacuum drying was 9.74 logo-CFU/g. After 5 days of storage at 4° C., the level reduced to 8.09 $\log_{10}$ CFU/g, which corresponds to probiotic survival of 83%.

Comparative Example 4

Survival of Bifidobacterium lactis BB12 in a Comparative Microparticle

Microparticles containing Bifidobacterium lactis BB12 and trehalose were prepared in accordance with Example 7. However, the Microparticle Precursor Composition used to prepare the microparticles for this Comparative Example had the following composition, for 400 g of composition: 200 g of melted concentrate of Bifidobacterium lactis BB12, 5% trehalose, 1% lecithin, 2% sodium alginate and 0.2% TWEEN 80, with the remainder of the composition being water.

The wet microparticles were then mixed with maltodextrin and Hi-Maize® Resistant Starch in accordance with the following ratio on a weight basis: (wet microparticles: maltodextrin:Hi-Maize® Resistant Starch) 80:20:20. The microparticles were then vacuum dried at 40° C. for 24 hours prior to a study of Bifidobacterium lactis BB12 survival. The probiotic loadings are measured as colony forming units per gram (CFU/g).

The initial level of Bifidobacterium lactis BB112 after vacuum drying was 9.9 $\log_{10}$ CFU/g. After 5 days of storage at 4° C., the level reduced to 7.60 $\log_{10}$ CFU/g, which corresponds to probiotic survival of 90%.

Comparative Example 5

Survival of Lactobacillus casei Lc431 in a Comparative Microparticle

Microparticles containing Lactobacillus casei Lc431 were prepared in accordance with Example 6. However, the Microparticle Precursor Composition used to prepare the microparticles for this Comparative Example had the following composition, for 400 g of composition: 200 g of melted concentrate of Lactobacillus casei Lc431, 2% sodium alginate and 0.2% TWEEN 80, with the remainder of the composition being water.

These wet microparticles were stored a 4° C. for a study of Lactobacillus casei Lc431 survival. The initial level of Lactobacillus casei Lc431 was 12.62 $\log_{10}$ CFU/g. After 13 days of storage at 4° C., the level reduced by 5.42 $\log_{10}$ CFU/g to 7.2 $\log_{10}$ CFU/g. This corresponds to a probiotic survival of around 57%.

Comparative Example 6

Survival of Lactobacillus casei Lc431 in a Comparative Microparticle

Microparticles containing Lactobacillus casei Lc431 and trehalose were prepared in accordance with Example 6. However, the Microparticle Precursor Composition used to prepare the microparticles for this Comparative Example had the following composition, for 400 g of composition: 200 g of melted concentrate of Lactobacillus casei Lc431, 2% sodium alginate, 5% trehalose and 0.2% TWEEN 80, with the remainder of the composition being water.

These wet microparticles were stored a 4° C. for a study of Lactobacillus casei Lc431 survival. The initial level of Lactobacillus casei Lc431 was 9.44 $\log_{10}$ CFU/g. After one month of storage at 4° C., the level reduced by 2.74 $\log_{10}$ CFU/g to 6.70 $\log_{10}$ CFU/g. This corresponds to a probiotic survival of around 70%.

The rates of probiotic survival for Comparative Example 6, when compared to those for Comparative Example 5, illustrate the effect of trehalose on probiotic survival.

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integers or steps.

The reference in this specification to any prior publication (or information derived from it), or to any matter which is known, is not, and should not be taken as an acknowledgment or admission or any form of suggestion that that prior publication (or information derived from it) or known matter forms part of the common general knowledge in the field of endeavour to which this specification relates.

Many modifications will be apparent to those skilled in the art without departing from the scope of the present invention.

The invention claimed is:

1. A microparticle precursor composition comprising a blend of a probiotic, a cross-linkable reagent, a denatured protein, a polyol plasticizer, trehalose and a carrier, wherein the blend does not contain a cross-linking reagent.

2. The microparticle precursor composition according to claim 1, wherein the denatured protein comprises whey protein isolate.

3. The microparticle precursor composition according to claim 1, wherein the denatured protein comprises pea protein.

4. The microparticle precursor composition according to claim 1, wherein the polyol plasticizer is glycerol.

5. The microparticle precursor composition according to claim 1, wherein the blend further comprises an emulsion comprising a hydrophobic active.

6. A method of producing a microparticle precursor composition comprising:
blending together a denatured protein, a polyol plasticizer, trehalose and a carrier to produce a protective matrix precursor composition; and
blending together a probiotic, the protective matrix precursor composition and a cross-linkable reagent to form a blend,
wherein the blend does not contain a cross-linking reagent.

7. The method according to claim 6, comprising: blending the probiotic with the protective matrix precursor composition to form a probiotic-containing matrix precursor; blending an emulsion comprising a hydrophobic active with the probiotic-containing matrix precursor to form a probiotic-containing emulsion; and blending the probiotic-containing emulsion with a cross-linkable reagent.

8. A method of producing microparticles comprising: providing the microparticle precursor composition of claim 1 in a finely divided state; and exposing the finely divided microparticle precursor composition to a cross-linking reagent that reacts with the cross-linkable reagent of the microparticle precursor composition to form microparticles.

9. Microparticles produced according to the method of claim 8.

10. A microparticle precursor composition comprising a blend of a probiotic, a cross-linkable reagent, a denatured protein, a polyol plasticizer, trehalose and a carrier, wherein the blend does not contain a cross-linking reagent, and wherein the microparticle precursor composition is capable of forming microparticles that have a cross-linked matrix provided by reacting a cross-linking reagent with the cross-linkable reagent, said cross-linked matrix being intermingled with a protective matrix comprising the denatured protein, polyol plasticizer and trehalose.

11. The microparticle precursor composition according to claim 10, wherein the denatured protein comprises whey protein isolate.

12. The microparticle precursor composition according to claim 10, wherein the denatured protein comprises pea protein.

13. The microparticle precursor composition according to claim 10, wherein the polyol plasticizer is glycerol.

14. The microparticle precursor composition according to claim 10, wherein the blend further comprises an emulsion comprising a hydrophobic active.

* * * * *